(12) United States Patent
Tanahashi et al.

(10) Patent No.: US 7,795,010 B2
(45) Date of Patent: Sep. 14, 2010

(54) FRACTIONATOR AND METHOD OF FRACTIONATION

(75) Inventors: Kazuhiro Tanahashi, Shiga (JP); Ichiro Kumo, Shiga (JP); Nobuyuki Kuroki, Shiga (JP); Hiroyuki Sugaya, Shiga (JP); Satoko Yamada, Shiga (JP); Shigehisa Wada, Shiga (JP); Giman Jung, Kanagawa (JP); Toshihiko Kuroda, Kanagawa (JP); Shuji Sekiguchi, Tokyo (JP)

(73) Assignee: Toray Industries, Inc., Tokyo (JP)

( * ) Notice: Subject to any disclaimer, the term of this patent is extended or adjusted under 35 U.S.C. 154(b) by 774 days.

(21) Appl. No.: 10/586,678

(22) PCT Filed: Jan. 20, 2005

(86) PCT No.: PCT/JP2005/000638

§ 371 (c)(1),
(2), (4) Date: Jul. 20, 2006

(87) PCT Pub. No.: WO2005/070954

PCT Pub. Date: Aug. 4, 2005

(65) Prior Publication Data

US 2007/0244306 A1    Oct. 18, 2007

(30) Foreign Application Priority Data

Jan. 21, 2004  (JP) ............................ 2004-013253
Jan. 30, 2004  (JP) ............................ 2004-023080

(51) Int. Cl.
   *C12M 3/00*        (2006.01)
(52) U.S. Cl. ................ 435/287.3; 435/283.1
(58) Field of Classification Search ............... None
   See application file for complete search history.

(56) References Cited

U.S. PATENT DOCUMENTS

| | | | | |
|---|---|---|---|---|
| 4,863,609 | A | | 9/1989 | Schnabel et al. |
| 5,128,037 | A | | 7/1992 | Pearl et al. |
| 5,186,824 | A | * | 2/1993 | Anderson et al. ........ 210/198.2 |
| 5,407,581 | A | * | 4/1995 | Onodera et al. ........... 210/654 |
| 5,976,433 | A | * | 11/1999 | Komatsu et al. .............. 264/41 |
| 6,193,864 | B1 | * | 2/2001 | Leader et al. .......... 204/403.02 |
| 6,348,156 | B1 | * | 2/2002 | Vishnoi et al. ............. 210/739 |
| 7,018,847 | B2 | * | 3/2006 | Mendel-Hartvig et al. .. 436/518 |
| 7,074,327 | B2 | * | 7/2006 | O'Connor et al. ........ 210/198.2 |
| 7,514,075 | B2 | * | 4/2009 | Hedrick et al. ............. 424/93.7 |
| 7,682,833 | B2 | * | 3/2010 | Miller et al. ................. 436/165 |

| | | | |
|---|---|---|---|
| 2002/0197167 | A1 | * 12/2002 | Kornelsen .................... 417/53 |

FOREIGN PATENT DOCUMENTS

| | | |
|---|---|---|
| EP | 0 255 011 A2 | 2/1988 |
| JP | 58-40323 A | 3/1983 |
| JP | 58-94858 A | 6/1983 |
| JP | 59-116223 A | 7/1984 |
| JP | 63-87984 A | 4/1988 |
| JP | 4-330921 A | 11/1992 |
| JP | 7-133289 A | 5/1995 |
| JP | 8-9992 A | 1/1996 |
| JP | 9-510200 A | 10/1997 |
| JP | 2001-200000 A | 7/2001 |
| JP | 2001-524839 A | 12/2001 |
| JP | 2002-1068 A | 1/2002 |
| JP | 3297707 B2 | 4/2002 |
| JP | 2002-542163 A | 12/2002 |
| JP | 2003-130882 A | 5/2003 |
| WO | WO-95/24418 A1 | 9/1995 |
| WO | WO-97/32653 A1 | 9/1997 |
| WO | WO-00/61607 A1 | 10/2000 |

OTHER PUBLICATIONS

Anderson et al., Molecular & Cellular Proteomics, vol. 1, No. 11, pp. 845-867, (2002).
Tirumalai et al., Molecular & Cellular Proteomics, vol. 2, No. 10, pp. 1096-1103, (2003). XP002390543.
Ahmed et al., Proteomics, vol. 3, pp. 1980-1987, (2003).
Rothemund et al., Proteomics, vol. 3, pp. 279-287, (2003).

* cited by examiner

*Primary Examiner*—Ann Y Lam
(74) *Attorney, Agent, or Firm*—Birch, Stewart, Kolasch & Birch, LLP

(57) ABSTRACT

The following is disclosed: (1) a membrane fractionator including a filtration section, a concentrating section, a recovery section and a liquid feed pump, wherein a flow channel connecting the filtration section, concentrating section and recovery section to each other constitutes a closed circuitry; (2) a method of biocomponent separation, characterized in that a sample derived from biocomponents is fed into an antibody adsorption membrane separation system having an antibody capable of adsorbing specified protein internally accommodated in the middle or a rear part of a membrane separation system that in the absence of antibodies adsorbing proteins, exhibits a permeation ratio between human alpha1-microglobulin and human albumin of 1.5 to 1000, thereby separating part of the biocomponents; and (3) a method of protein fractionation, comprising bringing a solution containing two or more types of proteins and water into contact with a hollow yarn separation membrane to thereby attain protein fractionation, characterized in that the fractionation solution contains an organic solvent.

20 Claims, 4 Drawing Sheets

FRACTIONATOR AND METHOD OF FRACTIONATION

FIELD OF THE ART

The invention relates to a method and a device for obtaining a sample with a changed composition from a biological component-containing solution, particularly from a raw liquid such as human blood, plasma, urine, or the like by fractionating biological molecules such as protein of the solution, particularly the raw liquid. Specifically, aiming to make clinical proteome analysis possible, the invention relates to a fractionation method and a fractionation device for obtaining a solution with a changed composition of biological components by removing components inhibiting detection of trace components, particularly high molecular weight proteins.

PRIOR ART

Recently, proteome analysis research proteomics has begun to draw attention as postgenome research. Since it is a very likely supposition that proteins, gene products, are more directly linked with symptoms of diseases than gene, it has been highly expected that research findings and achievements of proteome analysis of thoroughly investigating proteins can widely be applicable for diagnosis and medical care. Moreover, it is highly possible to find many proteins causing diseases and factors relevant to diseases, which cannot be found by genome analysis.

High speed structural analysis is made possible by MS (mass spectrometer) and technically it has greatly contributed to rapid advancement of proteome analysis, and practical application of MALDI-TOF-MS (matrix assisted laser desorption ionization time-of-flight mass spectrometry) has enabled ultramicroanalysis of polypeptides to be performed at a high throughput, and that makes it possible to identify even trace proteins which have not be detected conventionally and accordingly becomes a powerful tool for searching factors relevant to diseases.

The first purpose of clinical application of the proteome analysis is to find biomarker proteins induced or eliminated by diseases. The biomarker behaves in relation to symptoms of diseases, so that it can be a marker for diagnosis and also highly possibly becomes a target for producing pharmaceuticals. That is, since the findings and achievements of proteome analysis are highly possibly applicable to find a diagnosis marker and a target for producing pharmaceuticals rather than specified gene, it can be said that proteome analysis becomes a key technology for diagnosis and medical care in the postgenome era and since the identified biomarker directly brings profits to patients, that is, evaluation of response to the pharmaceuticals and speculation of side effect expression, it can be said that this technique plays an important role to promote so-called tailor-made medical care (order-made medical care).

In the case proteome analysis (clinical proteomics) is to be introduced in clinical researches, it is required to quickly and reliably analyze a large number of samples and moreover, since each clinical sample is slight in the amount and very precious, it is required to quickly carry out the high resolution, high sensitivity, and highly functional measurement. Mass spectrometry has considerably propelled the analysis and the characteristics of mass spectrometers, that is, high sensitivity and high throughput have greatly contributed to the analysis. However, although the techniques and appliances have been improved swiftly, the present situation is not yet ready to simply and quickly carry out proteome analysis in a clinical field.

One of the causes is attributed to pretreatment of clinical samples. It is needed to fractionate and refine proteins of a clinical sample as pretreatment of mass analysis and the treatment still takes several days and the operation of the pretreatment is complicated and requires experiences and skills and that becomes a high obstacle against the clinical application. If diagnosis of a disease in the entire body and the symptom control are made possible with a small amount of blood and body fluid, it is remarkably useful, however, there are many challenging subjects to overcome due to the variation of proteins contained in plasma.

It is assumed that there are 100,000 or more kinds of human proteins and about 10,000 kinds of proteins are contained in serum and the concentration of the total proteins in the serum is about 60 to 80 mg/mL. The proteins contained in a human serum are albumin (molecular weight: 66 kDa), immunoglobulin (150 to 190 kDa), transferrin (80 kDa), haptoglobin (>85 kDa), and lipoprotein (several 100 kDa) and all of them exist respectively in a large amount (>mg/mL). On the other hand, many of physiologically active proteins such as peptide hormones, interleukin, and cytokine regarded to be biomarkers of symptoms and factors relevant to diseases exist in a trace (<ng/mL). The contents are no more than nano to pico level as compared with those of the high content components with high molecular weights. In terms of the size of proteins, 70% or less in all kinds of proteins have a molecular weight of 60 kDa or lower and the above-mentioned biomarker proteins existing in a trace are almost all included in this range (reference to Non-Patent Document No. 1). Since these proteins are partially excreted to urine through a kidney, not only blood but also urine may be used as a sample.

To carry out proteome analysis by general serologic investigation, it is at first essential 1) to remove high molecular weight components with a molecular weight of 60,000 or higher, which become obstacles to detection of trace components relevant to disease and 2) to recover separated trace components relevant to the diseases and having a molecular weight less than 60,000 as reliably as possible.

Presently, high performance liquid chromatography (LC) and 2-dimensional electrophoresis (2 dimensional-polyacrylamide gel electrophoresis: 2D-PAGE) have been employed as means of separation and removal of the high molecular weight proteins, however it takes a 1 to 2 of days only for LC and 2D-PAGE operation. The time needed for them is very long as compared with the analysis time, several minutes, for MALDI-TOF-MS and ESI-MS (electrospray ionization mass spectrometry) and the remarkable advantageous point that MS, an analysis means, has a high throughput cannot sufficiently be exhibited in the clinical proteome analysis. Therefore, it must be said that at the present moment, MS is insufficient in practical applications for the purpose of obtaining analysis results within a time as short as possible for diagnosis and medical care in medical treatment fields and it becomes a significant cause of difficulty of utilization of MS for the daily clinical investigations. Therefore, it is expected that promptness of diagnosis of the clinical investigations by clinical proteome analysis may remarkably be improved if the above-mentioned problems are solved. Practically, it has been desired to make devices and apparatuses available which can fractionate a very small amount of a simple and separate aimed proteins at a high speed in place of LC and 2D-PAGE.

Further, since LC and 2D-PAGE are applicable only for a very small amount of a sample, the amount of a biomarker contained in a sample obtained thereby is very small, it some-times occurs that no marker is detected even if protein analysis is carried out by MS analysis or 2-dimensional electrophoresis analysis is carried out in the case of the sample preparatory methods described above.

As already practically utilized products or disclosed techniques for means of removing a main object substance, albumin, there are a carrier in which an affinity ligand such as a blue dye is immobilized, a centrifugal tubular apparatus (reference to Non-Patent Document 2, Patent Document 1) for fractionating the high molecular weight components by centrifugal filtration, a method of fractionation by electrophoresis principle, a traditional precipitation method such as ethanol precipitation by Cohn, and a method of fractionation by chromatography (reference to Non-Patent Document No. 3). Further, products for simultaneously removing albumin and immunoglobulin G (IgG) are commercialized.

However, they all have problems such as insufficiency of the separation and fractionation capability, unsuitability for a very small amount of a sample, contamination of chemical agents to be obstacles for mass spectrometry, and scanty in reproducibility.

2D-PAGE and liquid chromatography are highly functional. However, they are complicated and time-consuming techniques and therefore, devices convenient and having high separation efficiency within a short time have been required. In these years, a method of using a gel, Affi-Gel Blue, (reference to Non-Patent Document No. 4) and a method of using "Gradiflow" system (reference to Non-Patent Document No. 5) are reported as effective and improved albumin removal methods, however no technique further simplified and highly efficient for separation has not been reported yet. Also, it cannot be denied that the Blue gel removes particularly only proteins with high molecular weights like albumin and at the same time also proteins to be subjected to proteome analysis. As a filtration apparatus in which a liquid can be circulated, a filtration apparatus comprising a housing packed with a spirally rolled plane membrane is disclosed (reference to Patent Document 2), however the separation capability of the apparatus as it is not sufficient. Further, to detect a trace of proteins at a high precision, contamination of foreign substances has to be prevented. The foreign substances may include those beside proteins and cells and microorganism besides the aimed substances. Further, in analysis of proteins of the serum of, for example, a patient, proteins of the serum of another patient become foreign substances. So far, no apparatus for which a countermeasure against the foreign substance contamination is performed has been made available.

With respect to a separation and recovery method of proteins from a protein solution by a separation membrane, Patent Documents 3 and 4 disclose methods. Patent Document 3 discloses only a method but not a practical apparatus having a structure indispensable for protein separation. Also, Patent Document 4 does not refer to a single separation apparatus provided with all of the indispensable constituent parts.

As disclosed in Patent Document 4, a technique of separating and refining aimed proteins by using a hollow fiber membrane has been known well. Although Patent Document 4 does not disclose directly, it is common to employ a method of separating an aimed substance in these separation techniques by connecting columns having membranes or columns filled with gel with a flow pump through a silicon tube; transporting a moving phase by the flow pump; leading a raw liquid containing the aimed substance into the columns; and thereby brining the liquid into contact with the membranes or column. In the case a plurality of different samples are treated, washing work is required to avoid contamination between respective analysis processes and consequently, it takes a time and in case, pathogens are contained in the samples, the pathogen leakage may occur during the treatment and it may possibly infect a worker with the pathogens.

Methods and apparatuses have been developed to solve those problems and accordingly, proteome analysis has been employed widely in medical researches and clinical medical treatment fields and it has been made possible to quickly carry out examinations and diagnosis at a high precision and thus the analysis is expected to be a strong tool for clarifying the causes of diseases for which no effective curing method is made available yet or which are hard to be cured so far or for developing diagnosing methods in early stages of these diseases.

Non-Patent Document No. 1. Anderson N L, Anderson N G, "The human plasma proteome: history, character, and diagnostic prospects)", proteomics (Molecular & Cellular Proteomics), USA, The American Society for Biochemistry and Molecular Biology, Inc., (2002) vol. 1. p 845-867:

Non-Patent Document No. 2. Radhakrishna S. Tirumalai et al., "Characterization of the low molecular weight human serum proteome", Molecular & Cellular Proteomics. The American Society for Biochemistry and Molecular Biology, Inc. (2003) vol. 2. p 1096-1103:

Non-Patent Document No. 3. The Japanese Biochemical Society, "New Biochemical Experiments, vol. 1", Proteins (1) separation. refining characteristics", TOKYO KAGAKU-DOZIN CO., LTD. (1990):

Non-Patent Document No. 4. N. Ahmed et al., "An approach to remove albumin for the proteomic analysis of low abundance biomarkers in human serum", Proteomics, (2003) vol. 3, p 1980-1987:

Non-Patent Document No. 5. D. L. Rothemund et al., "Depletion of the highly abundant protein albumin from human plasma using the Gradiflow", Proteomics, (2003), vol. 3, p 279-287

Patent Document No. 1. Japanese Patent Application National Publication (Laid-Open) No. 2002-542163:

Patent Document No. 2. Japanese Patent Application Laid-Open (JP-A) No. 04-330921:

Patent Document No. 3. JP-A No. 59-116223:

Patent Document No. 4. JP-A No. 7-133289:

Patent Document No. 5. JP-A No. 2003-130882:

Patent Document No. 6. JP-A No. 58-40323

Patent Document No. 7. Japanese Patent No. 3297707

DISCLOSURE OF THE INVENTION

Problems to be Solved by the Inventions

In view of the above state of the art, the aims of the inventions are to solve the following:

1) to provide a fractionation device for separating an aimed solute simply and quickly with little foreign substance contamination in a solution to be obtained from a raw liquid, which is a solution containing biological components and with scarce pollution outside of the system and 2) to provide a fractionation method and a fractionation device of biological components by efficiently removing high molecular weight proteins contained in a solution containing biological components

Means for Solving the Problems by the Inventions

There are means for solving the above-mentioned problems broadly classified into three inventions. The first invention is as follows.

(1) A fractionation device for separating solutes or some of the solutes in a raw liquid by a membrane comprising 1) a supply part for loading the raw liquid;

2) a filtration part for filtering some of the solutes in the raw liquid sent from the supply part;

3) a concentration part for concentrating the filtrate from the filtration part; and 4) a flow pump for sending a mobile phase introduced into the device at the time of fractionation and being characterized in that a circuit composed of the filtration part, the concentration part, and a flow channel connecting the filtration part and the concentration part is a closed circuit.

(2) The above-mentioned fractionation device further comprising 5) a recovery part for recovering the concentrated solution obtained in the concentration part and being characterized in that a circuit composed of the supply part, the filtration part, and a flow channel connecting the supply part and the filtration part and a circuit composed of the concentration part, the recovery part, and a flow channel connecting the concentration part and the recovery part are respectively closed circuits.

(3) The fractionation device as descried in one of the devices being characterized in that the total inner capacity of the closed circuit s is 50 mL or lower.

(4) The fractionation device as descried in one of the devices being characterized in that filtration apparatus is employed for the filtration part and the concentration part each.

(5) The fractionation device as descried in one of the devices being characterized in that the filtration apparatus is a module having hollow fiber membranes.

(6) The fractionation device as descried in one of the devices being characterized in that the flow channel connecting the supply part and the filtration part is provided with a pump.

(7) The fractionation device as descried in one of the devices being characterized in that the recovery part is a container for sampling a concentrated liquid.

(8) The fractionation device as descried in one of the devices being characterized in that a buffer part for buffering the volumetric alteration at the time of loading the raw liquid is installed at any position in the circuits.

(9) The fractionation device as descried in one of the devices being characterized in that at least a portion of the circuit composed of the supply part, the filtration part, the concentration part, the recovery part, and flow channels connecting the respective parts is assembled in a cartridge.

(10) The fractionation device as descried in one of the devices being characterized in that the flow pump is a tube pump provided with a rotating rotor and a roller installed in a rotating manner in the outer circumference of the rotor and a portion of the outer wall of the cartridge is a squeezing member for squeezing a part of the circuit.

(11) The fractionation device as descried in one of the devices being characterized in that the fractionation device is provided with a transportation mechanism for transporting the cartridge in the direction to and from the rotor of the roller type tube pump to squeeze a flow pipe.

(12) The fractionation device as descried in one of the devices being characterized in that the raw liquid is a body fluid or a biological component-containing solution.

(13) A fractionation device comprising a cartridge and a roller type tube pump for separating solutes or some of the solutes in a raw liquid by a membrane and being characterized in that the cartridge comprises at least a portion of a circuit having at least a supply part for loading the raw liquid, means connected with the supply part by a flow channel for fractionating solutes of the raw liquid by a membrane, and a recovery part connected with the means for fractionating the solutes for recovering the fractionated solutes and the circuit is a closed circuit and a part of the outer wall of the cartridge is a squeezing member for squeezing the tube of the roller type tube pump and a part of the circuit is formed in a part of the outer wall of the squeezing member.

(14) A pipeline of a fractionation device for separating solutes or some of the solutes from a raw liquid by a membrane, including at least a portion comprising a supply part for loading the raw liquid, means connected with the supply part by a flow channel for fractionating solutes of the raw liquid by a membrane, and a recovery part connected with the means for fractionating the solutes for recovering the fractionated solutes in a cartridge, and being characterized in that the circuit is a closed circuit and a part of the outer wall of the cartridge forms a squeezing member and a tube forming a part of the circuit is installed in a portion of the outer wall of the squeezing member.

The second invention is disclosed as follows.

(1) A biological component separation method for separating some of biological components by supplying a biological component-derived sample to an antibody-adsorbing-membrane separation system containing, in a middle or a rear part of the membrane separation system, an antibody capable of adsorbing specified proteins and having a permeation ratio of human $\alpha 1$ microglobulin and human albumin (permeability of human $\alpha 1$ microglobulin/permeability of human albumin) in a range from 1.5 or higher to 1000 or lower under a condition that no antibody adsorbing proteins exists in the system and being characterized in that the concentration of proteins obtained by the separation is 10% or lower in 100% concentration achieved by the membrane separation system in the condition that no antibody exists.

(2) The above-mentioned biological component separation method being characterized in that the specified proteins may be serum albumin, immunoglobulin G, immunoglobulin A, immunoglobulin M, transferrin, haptoglobin, $\alpha_1$-antitrypsin, $\alpha_2$-macroglobulin, $\alpha_1$-acid glycoprotein, fibrinogen, complement C1q, complement C3, complement C4, complement C8, complement C9, complement factor B, apolipoprotein A, apolipoprotein B, Lp(a), collagen, myosin, actin, cytokeratin, keratin, and/or fibronectin.

(3) The above-mentioned biological component separation method being characterized in that the antibody is polyclonal antibody, monoclonal, or their fragments containing the antigen recognition sites.

(4) The above-mentioned biological component separation method as described in one of the methods, being characterized in that the antibody is fixed in the membrane surface of the membrane separation system.

(5) The above-mentioned biological component separation method as described in one of the methods, being characterized in that the membrane separation system comprises columns containing separation membranes therein and arranged in multi-steps in series and the antibody is fixed in the surface in the raw liquid side of the separation membrane of the column in the first stage.

(6) The above-mentioned biological component separation method as described in one of the methods, being characterized in that the membrane separation system comprises columns containing separation membranes therein and arranged in multi-steps in series and the antibody is fixed in the surface in the permeation side of the separation membrane of the column in the first stage.

(7) The above-mentioned biological component separation method as described in one of the methods, being characterized in that the membrane separation system comprises columns containing separation membranes therein and arranged in multi-steps in series and the antibody exists in the mobile phase in the flow channel between the membrane of the column in a prior stage and the membrane of the column in a posterior stage.

(8) The above-mentioned biological component separation method as described in one of the methods, being characterized in that the membrane separation system comprises columns containing separation membranes therein and arranged in multi-steps in series and the antibody is fixed in the flow channel between the membrane of the column in a prior stage and the membrane of the column in a posterior stage.

(9) A biological component separation method comprising a membrane separation apparatus having the permeation ratio of human α1 microglobulin and human albumin having a molecular weight of 60,000 in a range from 2 or higher and 1000 or lower and an antibody treatment apparatus containing an antibody in the middle or in the rear side of the flow channel of the membrane separation apparatus.

The third invention is as follows.

(1) A protein fractionation method for fractionating proteins on the basis of the molecular weights of the proteins by bringing a solution containing a plurality of kinds of proteins and water into contact with a hollow fiber separation membrane and being characterized in that the solution to be subjected to the fractionation contains an organic solvent.

(2) The protein fractionation method as described above being characterized in that the content of the organic solvent is 1% by volume or higher and less than 20% by volume.

(3) The protein fractionation method as described in one of the methods being characterized in that the organic solvent is acetonitrile.

(4) The protein fractionation method as described in one of the methods being characterized in that the fractionation is carried out at 30° C. or lower.

EFFECTS OF THE INVENTION

Owing to the employment of the closed circuit apparatus, the fractionation device disclosed as the first invention can simply and efficiently carry out fractionation of high molecular weight proteins such as albumin from a raw liquid, particularly from a body fluid such as serum in a short time while preventing contamination of the analysis sample (recovered liquid of the fractionation device) and biohazard. Further, in the device of the invention, a portion of the device is disposed in a cartridge, the fractionation process of a next sample can easily be started.

According to the second invention, proteins with high molecular weights are efficiently removed from a solution containing a plurality of proteins with different molecular weights and a solution enriched with a trace of low molecular weight proteins can be obtained to make it possible to easily detect these low molecular weight proteins by mass spectrometry.

According to the third invention, proteins with high molecular weights are efficiently removed from a solution containing a plurality of proteins with different molecular weights and a trace of low molecular weight proteins can be recovered at a high efficiency.

EXPLANATION OF SYMBOLS

Figure 1:
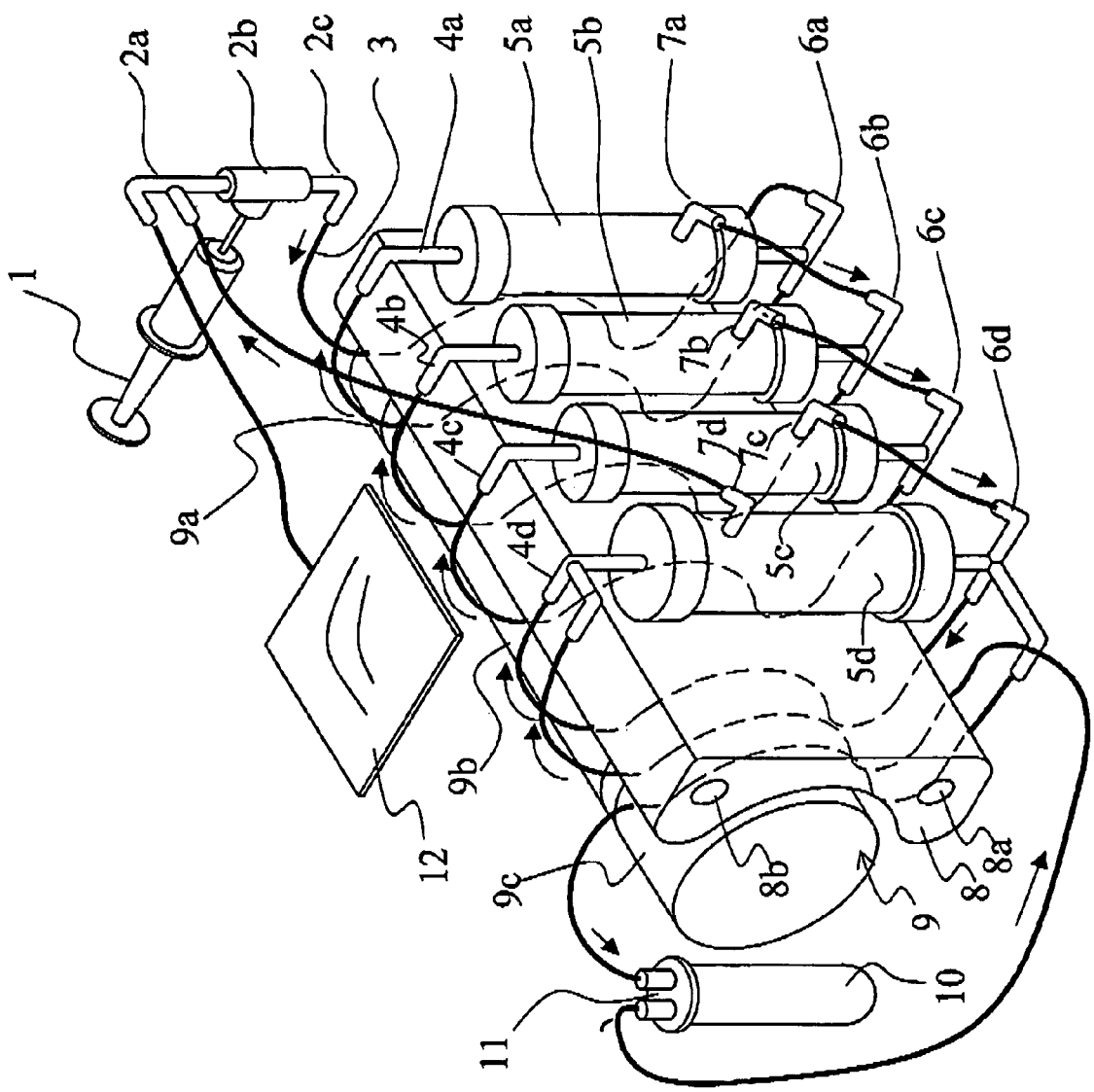
FIG. 1. A perspective view of a device used for Example 1 (for the first invention).

1: a syringe
2a: a three-way joint
2b: a rubber button (supply part)
2c: a joint
5a, 5b, 5c: a hollow-fiber membrane module of a separation part
5d: a hollow-fiber module of a concentration part
6a, 6b, 6c, 6d: a lower nozzle
7a, 7b, 7c, 7d: a lower nozzle of a trunk part
8: a squeezing member
8a: a guide axis
8b: a guide axis
9: a multi-channel type rotary roller
9a: a rotary roller
9b: a rotary roller
9c: a rotary roller
10: a recovery container
11: a recovery container cap
12: a back equipped with a tube
14: a cartridge
M: the entire body of a fractionation device
15: a three-way valve
16: a solution circulating flow channel
17a, 17b, 17c: a flow pump
18: a permeated solution outlet
19: membrane separation module
20: a filtrate outlet
21: an adsorption module
22: a filtrate outlet
23: a concentration module

BEST MODES OF THE EMBODIMENTS OF THE INVENTION

At first, the items in common among the respective inventions will be described.

The term "Fractionation" in this invention means separation of a solute contained in a solution and in the case a plurality of types of solutes are contained, it means separation of all or some of the solutes. In the case of preparation of a sample of proteome analysis of body fluid components by MS analysis method, aimed proteins to be recovered and proteins to be discarded are separated.

The body components in form of compounds may include proteins, nucleic acid, saccharides, lipids, vitamins, and inorganic salts and practically components of body fluids such as blood, serum, plasma, urine, lymph fluid, and cerebrospinal fluid.

The term "concentration" in this invention means removal of a solvent from a solution. In the aim of the invention, generally water is a solvent. It is allowed that a slight amount of a low molecular weight component is lost at that time.

Albumin may include albumin derived from human being, bovine, and other mammalian animals and birds. A high molecular weight component having a molecular weight higher than that of albumin may include mainly proteins with a molecular weight equal to or higher than the molecular weight (60,000 to 70,000) of albumin. Whether the molecular weight is equal to or higher than that of albumin can be determined by so-called SDS-PAGE (sodium dodecylsulphate-polyacrylamide gel electrophoresis) method. In the case the invention is specified by using albumin, it is preferable to define the invention with human albumin.

At first a group of the inventions belonging to the first invention will be described.

A preferable embodiment of the fractionation device of the first invention comprises 1) a supply part for loading the raw liquid;

2) a filtration part for filtering some of the solutes in the raw liquid sent from the supply part;

3) a concentration part for concentrating the filtrate from the filtration part; and 4) a flow pump for sending a moving phase introduced into the device at the time of fractionation and is characterized in that a circuit composed of the filtration part, the concentration part, and a flow channel connecting the filtration part and the concentration part is a closed circuit. Owing to the closed circuit formation, contamination and biohazard can be prevented.

A preferable embodiment of the above-mentioned fractionation device further comprising 5) a recovery part for recovering the concentrated solution obtained in the concentration part and being characterized in that a circuit composed of the supply part, the filtration part, and a flow channel connecting the supply part and the filtration part and a circuit composed of the concentration part, the recovery part, and a flow channel connecting the concentration part and the recovery part are respectively closed circuits.

Owing to the above-mentioned structure, an aimed solution can be obtained in the recovery part without contamination.

The device of the first invention is provided with the supply part for loading a raw liquid. The structure of the supply part may be equipped with a rubber button or a three-way valve. The raw liquid is supplied to the supply part such as a rubber button or the three-way valve from a syringe pump, an injector, or a raw liquid bag. These supply means are preferable in terms of the high closing property and controllability of the supplying speed. With respect to the supplying speed of the raw liquid, if the supplying speed is too high, the pressure of the closed circuit is increased and leakage of the liquid or membrane breakage is caused because of the increased of the pressure in the closed circuit. On the other hand, if the speed is too slow, it takes a long time to treat the raw liquid.

In the case of loading the raw liquid to the supply part from an outside of the closed circuit, alteration of the volume equal to the volume of the supplied raw liquid is caused in the circuit. If there is no part which can absorbs the alteration of the volume, excess pressure may be applied to the circuit or the membrane. Therefore, it is preferable to install a buffer part for absorbing the volumetric alteration at any position in the circuit. A mechanism such as a bag or a syringe equipped with a piston connected air-tightly via a T-shape connector is preferable to be used.

The supply part and the filtration part are connected to each other through a flow channel. Generally, it is preferable to install a flow pump for transportation in the flow channel. Some of solutes are filtered by the filtration part.

In the filtration part of the device of the invention, a filtration apparatus is preferable to be used and a filtration module containing a hollow fiber membrane or plane membrane is more preferable to be used. With respect to the molecular fractionation capability of the membrane, a membrane having a proper molecular fractionation capability (cut-off value) may be selected in consideration of the molecular weight of a solute to be recovered and the molecular weight of a solute to be removed.

It is also preferable for the filtration module to have a raw liquid inlet and a raw liquid outlet in the raw liquid side of the membrane and a filtrate component outlet in the filtration side of the membrane. It is preferable that a flow channel is composed by respectively connecting the raw liquid inlet and the raw liquid outlet with a tube, installing a flow pump in the flow channel, and accordingly circulating the object liquid to be treated in the raw liquid side of the membrane in the module by the pumps. Therefore, the object liquid to be treated is repeatedly subjected to the filtration process.

To improve the separation efficiency, filtration modules may be connected in series in a multi-steps in the filtration part. In the case of a multi-steps, the first filtration module near to the supply part is connected with the supply part via a flow channel in the middle of the flow channel connecting the raw liquid inlet and the raw liquid outlet. The flow channel from the filtered component outlet of the first filtration module is connected with the middle of the flow channel connecting the raw liquid inlet and the raw liquid outlet of the next filtration module. The flow channel of the next filtration module connected to the filtered component outlet is connected similarly to the raw liquid side flow channel of the next but one module. The function of the filtration part of the last filtration module is terminated, however the flow channel connect to the filtered component outlet is connected to the next concentration part. Accordingly, the filtrate from the filtration part is sent to the concentration part.

In the case of modules connected in a multi-steps filtration, the pumps existing in the flow channels connecting the raw liquid inlets and the raw liquid outlets of the respective filtration modules may be operated by separate motive powers or may be operated concentrically by a single motive power. It is preferable to operate the device at a constant flow rate to send the raw liquid without stagnation and to obtain the maximum separation efficiency.

The solutes are generally classified in accordance with the molecular weight of the solutes in the filtration module. The separation membrane to be used for the filtration module may be a filter or a hollow fiber membrane containing one or more kind materials selected from a group consisting of cellulose acetate type polymers such as cellulose and cellulose triacetate; polycarbonates; polysulfone type polymers such as polysulfone and polyether sulfone; polymethacrylates such as poly(methyl methacrylate); polyacrylates, polyamide nylon; poly(vinylidene fluoride); polyacrylonitrile, polyesters, polyurethanes, polystyrenes, polyethylene, and polypropylene and use of these materials makes it possible to separate solute components further efficiently. All kinds of plane membrane type separation membranes (filters) such as plane filters and cartridge type filters and hollow-fiber separation membranes (hollow-yarn membranes) of hollow fibers may be used. One or more kinds of substances (ligands) selected from a group consisting of antibodies, their fragments, polyethyleneimine, aminomethylpyridine, polyphenol, blue dye, a divalent metal ion (e.g., $Zn^{2+}$, $Ni^{2+}$, $Co^{2+}$, $Cu^{2+}$, or the like), and a hydrophobic compound (e.g., compounds with methyl group, benzyl group, phenyl group, chloromethyl group, octyl group, lauryl group or the like) may be fixed in these filters or hollow fibers, so that the filters or the hollow fibers can provided with affinity to the solutes. In the case the device is used for pretreatment of a sample for MS analysis, a function for adsorbing and removing unnecessary proteins for MS analysis can be provided.

The separation membrane to be used for the filtration module of the invention is particularly preferably a hollow fiber membrane because it has a wide surface area per the amount of a liquid to be treated and a low pressure loss in the process. Hollow fiber membrane modules, which are filtration apparatuses provided with a hollow fiber membrane, have been conventionally widely used as an artificial kidney (a dialysis module) relevant to proteins and all have been used for keeping proteins such as albumin without leakage and leaking low molecular weight components such as creatinine and urea and thus purifying blood flowing in the inner hollow side of the hollow fibers. On the other hand, the separation membrane to be used in the filtration part of the first invention is used for aiming to collect filtered components from the raw liquid side for analysis. Practically, it is preferable to leak protein components with a molecular weight as low as 5 kDa or lower, while high molecular weight components such as albumin are left in the raw liquid side.

Next, the flow channel from the last filtered component outlet of the separation part is connected to the concentration part. Also in the concentration part, it is preferable to use a filtration apparatus. With respect to the fractionation capability relevant to the molecular weights of the filtration apparatus to be employed, a membrane or an ultrafiltration membrane having a molecular weight fractionation capability (cut-off value: 0.05 to 0.5 kDa or lower) that is sufficient to prevent permeation of peptides in physiological saline solution may be used. In the concentration part, a concentration module provided with a hollow fiber membrane or a plane membrane is preferable to be installed. Also in the filtration apparatus, a module containing a separation membrane therein is preferable to be used. As the membrane to be used for the concentration module is preferably used a hollow fiber membrane because of the reason same as described above, that is, high treatment capability and low pressure loss. Also, with respect to the concentration module, it is preferable to have a raw liquid inlet and a raw liquid outlet in the raw liquid side of the membrane and a filtered component outlet in the filtration side of the membrane. It is preferable that the raw liquid inlet and raw liquid outlet are formed using a tube as to form a flow channel and a flow pump is installed in or on the flow channel and an object liquid to be treated is circulated in the raw liquid side of the membrane in the module by the pump. Accordingly, the object liquid to be treated can be subjected repeatedly to the filtration process. A solvent or components with extremely low molecular weight, which are not object to be separated, come out of the filtered component outlet. Since it is desired to suppress the volumetric alteration in the device as much as possible, the components coming out of the filtered component outlet are preferable to be kept in the fractionation device. Therefore, it is preferable to connect a flow channel to the filtered component outlet and connect one side of the flow channel to the supply part or the circuit in the periphery of the supply part. Also in the flow channel, it is preferable to install a flow pump.

A flow channel of a module in the prior stage is connected to the flow channel connecting the raw liquid outlet and the raw liquid inlet of the separation module in the separation part and also to the flow channel connecting the raw liquid outlet and the raw liquid inlet of the concentration part and it is preferable that a flow pump is so installed as to send the liquid by the flow pump after the flow channel is connected and liquids are joined. As a result, the separation and concentration efficiency is further improved.

In the fractionation device of the first invention, the concentration part is connected to the recovery part for recovering the liquid concentrated in the concentration part. A container for recovery is generally used as the recovery part. In the case a concentration module is used for the concentration part and the raw liquid outlet and the raw liquid inlet are connected by a flow channel, the liquid circulated in the flow channel is an object to be recovered. It is preferable to install a flow pump also in the flow channel. Further, to form a closed circuit, it is preferable two flow channels are formed in the recovery part and one between the flow channels is preferably a flow channel to which a concentrated liquid is supplied from the concentration part as described above and the other channel is preferably installed to send air in the recovery container to the raw liquid side of the concentration part through a flow pipe.

In the fractionation device of the invention, the flow pumps installed based on necessity between the supply part and the separation part, in the separation part, the concentration part, and the recovery part, and among these parts may be operated independently or operated coaxially by a single motive power. In the case of coaxial operation, the operation speed and sequence of each part can properly be separated.

With respect to the fractionation device of the invention for accomplishing the aim, the flow channels formed in the circuit may be installed independently, however in order to attain the convenience and stability of their installation, it is preferable to compose the circuit of the fractionation device by assembling at least some of means for fractionation by membranes such as the supply part, the filtration part, and concentration part, the recovery part, and the flow channels for connecting the respective parts in a cartridge. Further, it is preferable to form a part of the outside of the cartridge as a squeezing member for a roller type tube pump. It is preferable to make the cartridge detachable from a rotor driving part of a flow pump or a supporting member of the pump. The cartridge and the content are further preferable to be disposable. It is most preferable that portions of the flow channel with which flow pumps of the supply part, the separation part, the concentration part, and the recovery part are to be set is exposed to the outer wall of the cartridge from the inside of the cartridge and that the tube which forms the exposed flow channel is squeezed by the rotor of a roller type tube pump. In this case, the raw liquid inlets and the raw liquid outlets of the respective modules installed in the filtration part and the concentration part are adjusted to be coincident with the direction in which the tube is attached to the squeezing member. The tube forming the flow channels connected to ports of the respective modules is enabled to circulate a liquid therein via the squeezing member. To keep the precision of the squeezing, the tube is preferable to be positioned near to the base side of the rotor driving shaft. If the precision is low, the tube cannot be pressed and quantitative supply becomes difficult. To simply and precisely install the cartridge in a main body, it is preferable to install means in the cartridge and a pump respectively for fitting them each other. For example, a guide hole is formed in one, and a guide shaft is formed in the other and the guide shaft is inserted into the guide hole to make fitting easily. Successively, the position of the squeezing member is fixed to keep a proper distance of the flow channel composed of a plurality of tubes from the rotary roller of the roller type tube pump. When the roller type tube pump is operated, the raw liquid in a plurality of the modules can be sent successively. If a storage box storing a plurality of modules and the squeezing member are previously united and a tube, which is a portion of the flow channel, is previously held on the squeezing member, attachment and detachment of these components to and from the roller pump part is made easy.

The material for the cartridge is not particularly limited and those made of plastics are preferable since they are easy to handle and transport and have high strength. The shape is not particularly limited, however it is preferable that a sufficient space to store columns and a liquid channel is kept in the inside and that the squeezing face of the squeezing member which is to be squeezed by the driving rotor of the flow pump is curved like an arc in the direction of receiving squeezing force. The contact surface area is increased if the squeezing face is curved and accordingly, stable flow rate can be guaranteed.

The solution sending function is completed by pinching the tube with the surface of the squeezing member of the cartridge and the roller installed in the rotating manner in the outer circumference of the driving rotor of the roller type tube pump and the liquids existing in the respective parts in the cartridge are circulated when the driving rotor is rotated in the circumferential direction. The tube is so installed as to be squeezed to the squeezing face of the outer sheath of the cartridge, however it is not necessarily needed for the tube to have a contact with the squeezing face. To prevent the tube from vibrating vertically to the squeezing direction, it is particularly preferable to install the tube just like an arc to the squeezing face curved like an arc in the outer sheath of the cartridge.

The cartridge may be pushed against the driving rotor manually, however, from a viewpoint of the safety of a worker, it is preferable to install a mechanism for moving the cartridge when the cartridge is installed and transporting the cartridge to the position where the rotor squeezes the tube installed in the cartridge.

In the case of fractionation by the fractionation device of the invention, the mobile phase is preferably water or an aqueous solution. Particularly, in the case the raw liquid is a body fluid and the solutes are proteins, a pH buffer solution is preferable to be used. Further, in the case a sample to be obtained by this device is to be subjected to a MS analyzer, it is preferable to use a buffer solution containing a volatile substance which does not inhibit the analysis and for example, ammonium carbonate, ammonium acetate, and ammonium formate are preferable to be used. The aqueous solution for the mobile phase may contain one or more substances selected from a group consisting of a surfactant, an emulsifier, an organic solvent, an alcohol, ethylene glycol, polypropylene glycol, polyethyleneimine, aminomethylpyridine, protamine sulfate, ammonium sulfate, polyphenol, blue dye, chaotropic salt, and a hydrophobic compound, so that coagulation of proteins, which are the high molecular weight components, is promoted to produce gigantic molecules and adsorption is thus promoted and leakage of the proteins out of the fractionation membrane is suppressed to efficiently cut off the high molecular weight components and improve the final separation efficiency. The surfactant (an amphoteric surfactant and an anionic surfactant) is effective to suppress mutual reaction among proteins and promote the molecular fractionation.

The above-mentioned ligand and solutes of the aqueous solution may be selected in consideration of the extent of the separation of the aimed proteins.

It is preferable to use a tube as the flow channel for connecting the respective constituent elements of the fractionation device of the invention and more preferable to used a softer and elastic body. For example, silicone resins, poly (vinyl chloride), polyurethanes, fluoro resins, natural rubbers, and synthetic rubbers are used preferably and silicon resins and fluoro resins are particularly preferable since they scarcely adsorb the aimed biological components.

The recovery container to collect the concentrated liquid of the invention is preferably made of a material which scarcely adsorbs aimed biological components and polypropylene, silicone resins, and fluoro resins are preferably used. Besides, polystyrene and glass may also be used and in that case, to suppress adsorption of the aimed biological components, those whose inner surfaces are subjected to treatment for suppressing the adsorption of the biological components are preferable. The treatment for suppressing the adsorption is, for example, hydrophilic treatment and practically plasma treatment, coating with a hydrophilic polymer and surface grafting can be employed.

The fractionation device of the invention is suitable for separating biological molecules from a raw liquid containing biological components, particularly human plasma, serum, urine, saliva, tear fluid, cerebrospinal fluid, ascites, pleural fluid, amniotic fluid, and lymph. The sizes of the respective filters and hollow fiber membrane modules and the flow speeds of the refluxed liquids are properly determined, depending on the quality and the quantity of a biological material to be a raw material such as plasma, urine or the like, however in general, if a module is too large, it cannot be handled easily and additionally, since the surface area of the module itself becomes large, it results in adsorption loss of trace components. If a module is too small, it becomes impossible to treat a large quantity of a sample. Particularly in the case of treatment of a sample in an amount of 0.1 to 100 mL, which is a practical volume in the clinical field, by a hollow fiber membrane, a cylindrical module with a diameter of 0.2 to 5 cm and a length of 3 to 20 cm is preferable to be used. Further, the total inner capacity of the closed circuit is preferably 50 mL or lower. In the case of execution of fractionation treatment in so-called on-the-table size, the amount of a sample is preferably 1 to 400 ml and more preferably 5 to 100 ml for serum. The fractionation is carried out at a flow rate preferably 0.1 to 20 mL/min and more preferably 0.2 to 10 mL/min.

A sample obtained finally in the recovery part by loading a raw liquid containing biological components into the fractionation device of the invention and operating the device is useful for analyzing various kinds of proteins by liquid chromatography, electrophoresis, MS, or the like and particularly useful for proteome analysis using electrophoresis and MS.

The MS to be employed for the analysis of a sample obtained by the fractionation device of the invention is not particularly limited and as an ionization part type, an electrospray ionization type, an atmospheric pressure ionization type, a high speed atom collision type, a quadrupole type, a cyclotron resonance type, a magnetic sector type, or a matrix-supporting laser breakdown ionization type part may be used in combination with a mass analysis part such as an ion trap type, a time-of-flight type, or a Fourier conversion type mass analysis part. In this case, MS may be used in the form of a tandem MS such as MS/MS and MS and FT-MS. In the case of a tandem MS, all types of MS are usable and particularly the efficiency is improved when MS is used in combination with the ion trap type, a quadrupole-time-of-flight (Q-TOF) type, and FT-MS.

Structural data of various kinds of protein components can be collected by analysis in combination with the device of the invention and the data include not only peptide-mass finger print (PMF) but also the primary structural data (aminoacid sequence) of respective peptides.

Next, the second invention will be described.

The second invention indispensably comprises the following:

1) a membrane separation system having a permeation ratio of human $\alpha 1$ microglobulin to human albumin (permeability of human $\alpha 1$ microglobulin/permeability of human albumin) in a range from 1.5 or higher to 1000 or lower under a condition that no antibody which adsorbs proteins exists in the system and 2) an antibody which adsorbs proteins is essentially required, and it is required that the concentration of the specified proteins obtained by the separation method of the invention is 10% or lower in 100% concentration achieved by the membrane separation system in the condition that no antibody exists. Herein, $\alpha_1$ microglobulin represents proteins with a molecular weight of 30,000 or lower and human albumin represents proteins with a molecular weight of 60,000 or higher.

For example, a serum is used as a sample, since albumin and immunoglobulin exist in high concentration in the serum, these proteins cannot completely be separated even if a membrane is used and some leak out of the membrane. Further, the sample also contains fragment peptides having a low molecular weight and produced by decomposition of the proteins and such peptides cannot be separated by the membrane and therefore it is desired to remove them by an antibody. The leaking proteins and their fragment peptides inhibit detection of a trace of components by mass spectrometry. Separation by the invention makes it possible to decrease the leaking proteins to 1/10 and increase the sensitivity of the mass spectrometry and detect a trace of components. In the second invention, a membrane separation system is used. As a membrane to be used for the separation is used generally porous membranes and any kind of plane membrane type separation membranes (plane membranes) such as a plane filter and a cartridge type filter and a hollow separation membrane (hollow fiber membrane) of hollow fiber may be used. Generally, a hollow fiber has a wide surface area per the amount of a liquid to be treated and a low pressure loss and therefore it can be used most efficiently. Also, the plane filter has an advantageous point that the membrane is easy and economical to be formed. As a material to be used for the membrane is exemplified one or more kinds of materials selected from a group consisting of cellulose, cellulose acetate, polycarbonate, polysulfones, polymethacrylates such as poly(methyl methacrylate), polyacrylates, polyamides, poly(vinylidene fluoride), polyacrylonitriles, polyesters, polyurethanes, polystyrenes, polyethylene, and polypropylene. Among them are polysulfones which have been used widely for dialyzers preferable since they have good fractionation capability.

The separation capability of the membrane separation system of the invention is defined as a permeation ratio of human $\alpha 1$ microglobulin to human albumin (permeability of human $\alpha 1$ microglobulin/permeability of human albumin) in a range from 1.5 or higher to 1000 or lower under a condition that no antibody exists in the system. The preferable ratio is 2 or higher. That the permeation ratio is lower than 1.5 means that the membrane pore diameter is so large as to pass all kinds of proteins regardless of the molecular weight or that the membrane pore diameter is so small as to prevent any kind protein regardless of the molecular weight and in this range, the membrane cannot work practically as a membrane. It is more desirable as the permeation coefficient is higher, however actually, the permeation coefficient is sufficient if it is 1,000.

The membrane separation system in the invention is for fractionating the aimed proteins from a sample containing proteins, particularly a sample derived from blood such as serum. Particularly, the system may be those carrying out fractionation process of fractionating proteins such as human $\alpha 1$ microglobulin with a molecular weight of 30,000 or lower by a membrane in a single step or in multi-steps.

It is particularly preferable to use a hollow fiber membrane module for the membrane separation system of the invention. Hollow fibers have been conventionally widely used as an artificial kidney (a dialysis module) relevant to proteins and all have been used for keeping proteins such as albumin without leakage and leaking low molecular weight components such as creatinine and urea and thus purifying blood flowing in the inner hollow side of the hollow fibers. On the other hand, the hollow fibers are used in the invention for collecting fractions leaking out of the inner hollow part of the hollow fibers for analyzing the fractions and they are used in a manner for keeping high molecular weight components such as albumin in the inner hollow parts of the hollow fibers and at the same time leaking the protein components with a molecular weight of 30,000 lower such as $\alpha 1$ microglobulin.

In this invention, the proteins to be adsorbed in the antibody are proteins existing in a concentration as high as 1 μg/mL or higher in a sample to be treated and in the case the sample is blood, serum, or plasma, examples are serum albumin, immunoglobulin G, immunoglobulin A, immunoglobulin M, transferrin, haptoglobin, $\alpha_1$-antitrypsin, $\alpha_2$-macroglobulin, $\alpha_1$-acid glycoprotein, fibrinogen, complement C1q, complement C3, complement C4, complement C8, complement C9, complement factor B, apolipoprotein A, apolipoprotein B, Lp(a), keratin, and collagen and in the case the sample is cell extract, examples are myosin, actin, cytokeratin, keratin, and/or fibronectin.

The antibody to be used may be a monoclonal antibody and a polyclonal antibody. Further, it may have any morphology if it includes antibody fragments such as Fab or F(ab)' and antigen recognition portion.

The antibody in the invention may be built in the middle of or behind a flow channel of the membrane separation system in any optional morphology. It may exist in a flow channel of the membrane separation system while being dissolved or dispersed in a solution or fixed in the inner surface and/or the outer surface of the membrane. It may be fixed in spherical beads, a woven fabrics, or a nonwoven fabric installed in a flow channel. A column filled with a carrier in which the antibody is fixed may be installed in a flow channel.

In the case the membrane separation system comprises columns containing separation membranes and arranged in multi-steps in series, an antibody can be fixed in the surface of the separation membrane of the first step column in the raw liquid side and/or the surface in the permeation side or in the surface of the separation membrane of the second step column in the raw liquid side and/or the surface in the permeation side. The antibody may be fixed in the mobile phase liquid in the flow channel between the membrane in the prior stage and the membrane in the column in the next stage.

The amount of the antibody to be disposed may be optional and it may be determined in accordance with the amount of the proteins leading out of the membranes of the membrane separation system. The amount of the leaking proteins may approximately be determined in accordance with the content of the high concentration proteins contained in the sample to be treated and the sieving coefficient and treatment time of the proteins by the membranes. If the amount of the antibody is too small, the proteins cannot be removed by adsorption and on the contrary, if the amount is too high, the membranes are clogged and a sufficient separation function cannot be obtained in the case the antibody is fixed in the membranes or exists in free state in the raw liquid side of the membranes.

The second invention includes a device for carrying out the separation method of the invention. That is, the invention includes a biological component separation device comprising a membrane separation device having a permeation ratio of human α1 microglobulin to human albumin (permeability of human α1 microglobulin/permeability of human albumin) in a range from 1.5 or higher to 1000 and an antibody treatment apparatus containing an antibody and installed in the middle of or behind the flow channel of the membrane separation apparatus.

Preferable embodiments of the separation method using the membrane separation system of the invention are as follows.

The function of the membrane separation system is to separate proteins having a molecular weight of 60,000 or higher such as albumin to be discharged from a sample and proteins having a molecular weight of 30,000 or lower such as α1 microglobulin, aimed proteins to be recovered, by a membrane. The system comprises a porous membrane having a molecular sieving effect for a plane filter or a membrane of the hollow fiber membrane module and carries out molecular fractionation by the separation and sieving with the membrane. Use of the hollow fibers is particularly effective since the fractionation membrane surface area is considerably increased.

The material of the membrane to be used in the invention is not particularly limited, however one or more kind materials containing polymers selected from a group consisting of cellulose, cellulose acetate, polycarbonates, polysulfones, polymethacrylates such as poly(methyl methacrylate), polyacrylates, polyamides, poly(vinylidene fluoride), polyacrylonitrile, polyesters, polyurethanes, polystyrenes, polyethylene, and polypropylene may be employed. With respect to the membrane structure, both having a sponge structure almost an uniform structure and having a double structure of a dense layer and a support layer having a high porosity and a high membrane strength may be used. The surface properties of the membrane are determined in accordance with the properties of proteins to be separated and may be hydrophilic or hydrophobic.

In the case of a hydrophilic membrane, the hydrophilic membrane may include those produced by copolymerizing hydrophilic monomers and hydrophobic monomers or blending and film-forming hydrophilic polymers and hydrophobic polymers; those produced by bonding or sticking hydrophilic polymers to the surfaces of membranes of hydrophobic polymers; and those produced by chemically treating, plasma treating or radiation-treating the surfaces of membranes of hydrophobic polymers and if the surfaces are made hydrophilic, the method for the treatment is not particularly limited. The hydrophilic components are not particularly limited and preferable examples may include hydrophilic polymers, e.g., polyalkylene oxides such as polyethylene glycol, polyvinylpyrrolidone, polyvinyl alcohol, poly(hydroxyethyl methacrylate), and polyacrylamide. These hydrophilic membranes are effective to suppress adsorption of needed proteins and recover them without vain loss.

Further, materials in which one or more of polyethyleneimine, aminomethylpyridine, polyphenol, Blue dye, a divalent metal ion ($Zn^{2+}$, $Ni^{2+}$, $Co^{2+}$, $Cu^{2+}$, or the like), and a hydrophobic compound (i.e. compound with methyl group, benzyl group, phenyl group, chloromethyl group, octyl group, lauryl group or the like) are fixed may also be used.

With respect to the molecular fractionation capability of the membrane, membranes having a molecular weight fractionation capability (cut-off value: 30 to 60 kDa or lower) that is sufficient to prevent permeation of 50% or more albumin in physiological saline solution may be used.

In the membrane separation system of the invention, in addition to the above-mentioned means for filtering the low molecular weight proteins, means for a concentration step may be installed. In the means, a porous membrane having a molecular sieving effect may be used for a plane filter or a membrane of the hollow fiber membrane module and concentration is carried by the separation and sieving with the membrane. In the case the amount of a sample is a little, it is effective to use a concentration device comprising a plane filter attached to a centrifugal tube and in the case of a large amount of a sample, it is effective to use hollow fibers.

In this step, it is preferable to use a porous membrane having a molecular sieving effect for a plane filter or a membrane of the hollow fiber membrane module and to carry out concentration by the separation and sieving with the membrane. In the case the amount of a sample is a little, it is effective to use a concentration device comprising a plane filter attached to a centrifugal tube and in the case of a large amount of a sample, it is effective to use hollow fibers.

The material of the membrane to be used for the above-mentioned purpose is not particularly limited, however one or more kind materials containing polymers selected from a group consisting of cellulose, cellulose acetate, polycarbonates, polysulfones, polymethacrylates such as poly(methyl methacrylate), polyacrylates, polyamides, poly(vinylidene fluoride), polyacrylonitrile, polyesters, polyurethanes, polystyrenes, polyethylene, and polypropylene may be employed. With respect to the membrane structure, both having a sponge structure almost an uniform structure and having a double structure of a dense layer and a support layer having a high porosity and a high membrane strength may be used.

With respect to the molecular fractionation capability of the membrane, it is preferable to use a membrane having a molecular weight fractionation capability (cut-off value: 10 to 1000 or lower) or an ultrafiltration membrane that is sufficient to prevent permeation of peptides in physiological saline solution may be used. In the case an antibody which adsorbs specified proteins is supplied to the middle of or behind the above-mentioned membrane separation system, the antibody is not particularly specified if it is treated during the membrane fractionation process or at a position where the liquid obtained in the membrane fractionation process is brought into contact with it. It is preferable that the antibody fixed in beads or gel is packed in a portion or the entire body of the circuit and for example as a common method, a column filled with gel in which the antibody is fixed is installed in a portion of the circuit. It is also preferable to fix the antibody in the plane filter or the membrane of the hollow fiber membrane module.

A method for supplying the antibody to the support is not particularly limited and examples of the method for efficiently fixing the antibody may be a method of fixation of the antibody in a substrate by chemical reaction using —$NH_2$ end of the antibody; a method of fixing oxidized saccharide; and a method of fixation of the antibody in ligands of protein A and protein G. The antibody to be used may be polyclonal antibody and monoclonal antibody without any limit. The proteins composing the antibody are preferably immunoglobulin and immunoglobulin G is more preferable.

In the case the antibody is stuck to a supporting body and loaded together with the supporting body, the material of the supporting body is not particularly limited and examples to be used preferably for the materials are materials selected from a group consisting of cellulose, cellulose acetate, polycarbonates, polysulfones, polymethacrylates, polyacrylates, polyamides, poly(vinylidene fluoride), polyacrylonitriles, polyesters, polyurethanes, polystyrenes, polyethylene, and polypropylene. With respect to the membrane structure, both having a sponge structure almost an uniform structure and having a double structure of a dense layer and a support layer having a high porosity and a high membrane strength may be used.

The morphology of the material may include spherical beads, fibers, woven fabrics, nonwoven fabrics, plane type materials using staple, and hollow fibers and they are preferable to respectively have porous shapes with high surface roughness since the adsorption surface area can be increased. Also, in the case the separation membrane has morphology just like a plane membrane or a hollow fiber membrane, separation and adsorption can be carried out simultaneously and therefore the case is particularly preferable.

In the case the antibody is used while being stuck to a membrane, with respect to the properties of the membrane substrate itself, those which are made hydrophilic in order to suppress non-specific protein adsorption and those which are made hydrophobic in order to selectively adsorb high molecular weight proteins such as albumin may properly be selected and used for the respective fractionation and adsorption steps.

Examples of the membrane comprising a substrate made to be hydrophilic may be those produced by copolymerizing hydrophilic monomers and hydrophobic monomers or blending and film-forming hydrophilic polymers and hydrophobic polymers; those produced by bonding or sticking hydrophilic polymers to the surfaces of membranes of hydrophobic polymers; and those produced by chemically treating, plasma treating or radiation-treating the surfaces of membranes of hydrophobic polymers. The hydrophilic components are not particularly limited and preferable examples may include hydrophilic polymers, e.g., polyalkylene oxides such as polyethylene glycol, polyvinylpyrrolidone, polyvinyl alcohol, and poly(hydroxyethyl methacrylate). As the hydrophobic membranes, those produced by introducing hydrophobic components and those obtained by introducing hydrophobic ligands into membrane surfaces may be used. Examples of the hydrophobic components may be polymers composed of addition-polymerizable compounds having carbon-carbon double bond such as methacrylic acid esters, acrylic acid esters, olefins such as ethylene and propylene, acrylonitrile, and methacrylonitrile; polysulfones, and polymers of cellulose, however those which can be used as a membrane material can be used without any limit.

Further, materials in which at least one of compounds selected from polyethyleneimine, aminomethylpyridine, polyphenol, Blue dye, a divalent metal ion, and a hydrophobic aromatic compound is fixed may also be used.

In the separation method of the biological components of the invention, as a solution for developing in the system, a buffer solution is used preferably. Further, the adsorption or fractionation capability can be improved by adding various kinds of chemical agents. Practically, the solution may contain one or more substances selected from a group consisting of a surfactant, an emulsifier, an organic solvent, an alcohol, ethylene glycol, polypropylene glycol, polyethyleneimine, aminomethylpyridine, protamine sulfate, ammonium sulfate, polyphenol, blue dye, a chaotropic salt, and a hydrophobic compound.

For example, proper addition of ammonium sulfate, polyethylene glycol, polyethyleneimine, or a chaotropic salt promotes coagulation of proteins, which are high molecular weight components and accordingly produces gigantic molecules and consequently, adsorption is promoted and leakage of the proteins out of the fractionation membrane is suppressed to efficiently cut off the high molecular weight components. Meanwhile in the fractionation step, proper addition of a surfactant (an amphoteric surfactant and an anionic surfactant) is effective to suppress mutual reaction among proteins and promote the molecular fractionation.

The filtered fractions obtained in this step are subjected to the next concentration step. In the case the solution is sufficiently separated in the adsorption step and the repeated membrane separation step, this step may be omitted.

In the case the separation method of the biological components of the invention involves a plurality of steps, the respective units for carrying out these steps are connected one another through the flow channels and when they are operated continuously, continuous operation is easily and automatically performed. Of course, the respective steps may be operated independently. Pumps are installed in tubes and solutions are sent by the pumps and in the case of a small scale, the solution transportation may be carried out by a syringe and the concentration may be carried out by a spin column type device in the concentration step. Device elements for carrying out a plurality of steps and connected with one another through the flow channels may be used for the method. A device in which a hollow fiber membrane module capable of efficiently obtaining proteins with a molecular weight of 30,000 such as $\alpha_1$ microglobulin by filtration and a second hollow fiber membrane module for simultaneously carrying out adsorption of specified proteins and concentrating a protein solution are directly connected with each other by an aqueous solution flow channel is also included as a preferable device.

Introduction of the concentration step causes a further improved effect. The method may also involve repeating the step of fractionation of low molecular weight proteins by permeating them by the separation membranes; inserting the concentration step between the fractionation step by the separation membranes and the adsorption step; and carrying out permeation of the separation membranes with the proteins again after the adsorption step.

The separation method of the biological components of the invention is suitable for separating biological molecules from a blood-derived sample, particularly human plasma and serum. The sizes of the respective filters and hollow fiber membrane modules and the flow speeds of the refluxed liquids are properly determined, depending on the quality and the quantity of the sample and in the case of execution of fractionation treatment in so-called on-the-table size, the amount of the sample is preferably 1 to 400 ml and more preferably 5 to 100 ml for serum. The fractionation is carried out at a flow rate preferably 0.1 to 20 mL/min and more preferably 0.2 to 10 mL/min.

According to the second invention, high speed treatment can be carried out by the membrane separation system and the time to be taken is in a range from 1 to 6 hours for one time treatment and in terms of prevention of contamination and biohazard of the sample, it is possible to produce a series of devices disposable every time. Since appliances are repeatedly used in the analysis by an electrophoresis system or liquid chromatography, there is a risk of contamination with a sample and there is a problem on the reproducibility by regenerated analysis columns and also their operation is complicated and therefore, the analysis by an electrophoresis system or liquid chromatography is not necessarily suitable for frequent treatment of many samples.

The analysis sample obtained by the separation method of the biological component of the invention is useful for various protein analysis by liquid chromatography, electrophoresis, or MS and is particularly useful for proteome analysis by MS or electrophoresis. The MS to be joined directly or indirectly to the device of the invention is not particularly limited and an electrospray ionization type, an atmospheric pressure ionization type, a quadrupole (QQQ) type, a magnetic sector type, a time-of-flight type, a MS/MS, MSn, FT-MS type, an ion trap type or combination types of them are preferable. Also, a tandem MS such as MS/MS and MS. (e.g. MS3) are included. In the case of the tandem MS, all types of MS are usable and particularly the efficiency is improved when MS is used in combination with the ion trap type, a quadrupole-time-of-flight (Q-TOF) type, FT-MS and sector appliance combination of a quadrupole type and an ion trap type. Accordingly, selective detection of the peaks in the MS/MS and/or MSn analysis is made possible.

Structural data of various kinds of trace protein components can be collected by analysis in combination with the device of the invention and the data include not only peptide-mass fingerprint (PMF) but also the primary structural data (aminoacid sequence) of respective peptides.

Hereinafter, one embodiment of the separation method of the biological components of the second invention will be described with reference to the drawings.

Figure 3:
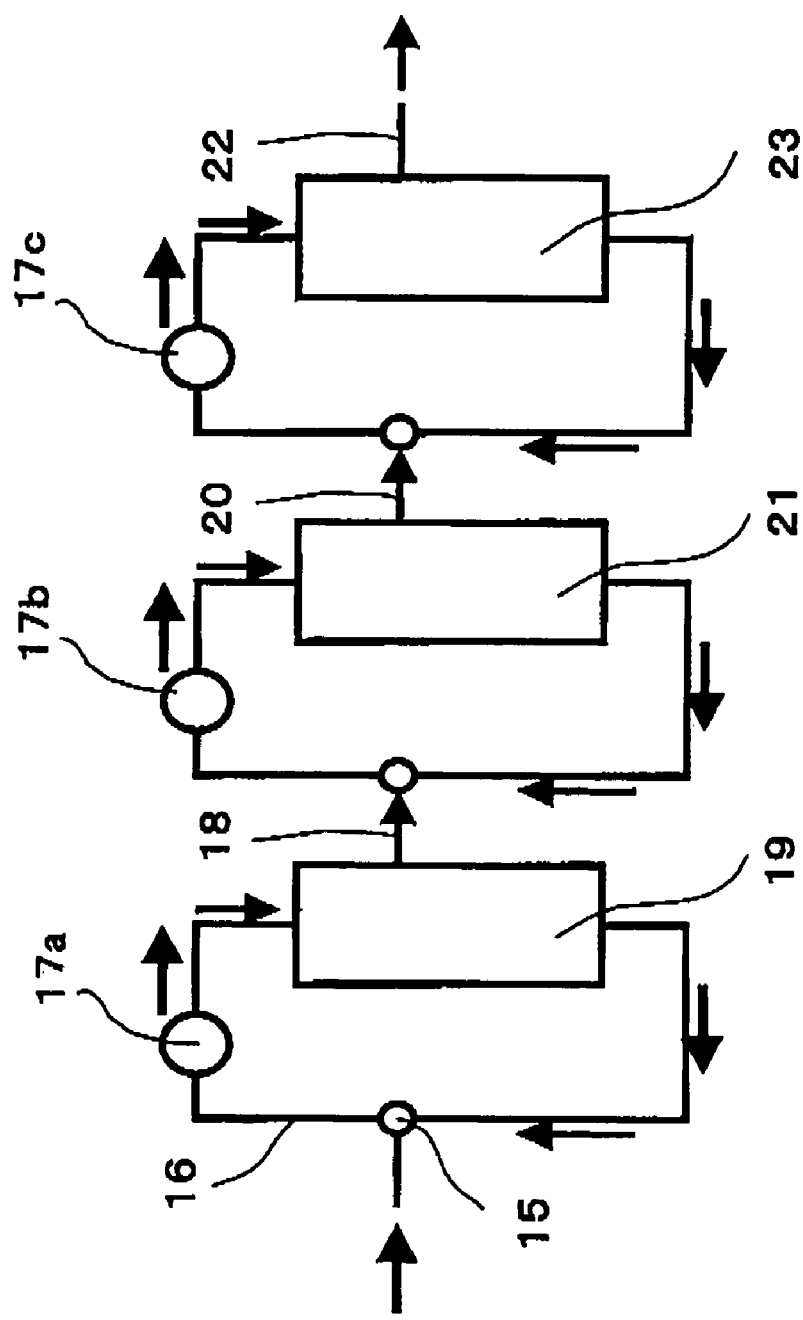
FIG. 3. A schematic view showing one embodiment of a biological component separation method of the second invention.

FIG. 3 is a conceptual drawing of an antibody component-adsorption membrane separation system of the invention and comprising a membrane separation element, an adsorption element, and a concentration element. The flow of a liquid is shown as an arrow. A sample of a material such as serum is injected into a membrane separation module 19, which is a first element, via a three-way valve 15 and sent and circulated in the solution circulation flow channel 16 made of a tube by a flow pump 17a. The filtrate produced in this process is obtained through a permeated liquid outlet 18. The permeated liquid obtained via the permeated liquid outlet 18 is loaded into an adsorption module containing a separation module in whose inner surface an antibody is fixed by a flow pump 17b and circulated. The permeated liquid which permeates the separation membrane installed in the adsorption module is obtained through a filtrate outlet 20. The permeated liquid is further circulated in a concentration module 23 containing a membrane for concentration by a flow pump 17c and water and proteins with very low molecular weight permeate the membrane and are discharged out a permeated liquid outlet. The solution remaining in concentration module 23 and the circulation flow channel is taken out to obtain a desired sample.

Finally, the third invention will be described.

The invention provides a protein fractionation method for fractionating proteins on the basis of the molecular weights of the proteins by bringing a solution containing a plurality of kinds of proteins and water into contact with a hollow fiber separation membrane and being characterized in that the solution to be subjected to the fractionation contains an organic solvent. Proteins are not only bonded with other proteins due to the mutual action of hydrophobicity but also adsorb on the material surface. The hydrophobic mutual action is inhibited by adding an organic solvent in the solution and accordingly the proteins with a high molecular weight are left in the raw liquid side and the proteins with a low molecular weight are permeated at a high efficiency.

In the separation method of the invention, an organic solvent is added. Addition of an organic solvent remarkably suppresses adsorption phenomenon of proteins to the separation membrane, the fluid channel such as the tube, and the container for recovering the fractionated solution. The concentration of the organic solvent in the invention is preferably in a range from 1% by volume or higher and less than 20% by volume, more preferably in a range from 3% by volume or higher and less than 19% by volume, and even more preferably in a range from 5% by volume or higher and less than 18% by volume. In the case of dilution of a high concentration protein solution with a buffer solution mixed with an organic solvent, if an excess amount of the organic solvent is added to the buffer solution, the protein solution are coagulated because of the effect of the solvent and further, in the case of protein fractionation is carried out with a hollow fiber membrane by the separation method of the invention in the pretreatment for proteome analysis of serum proteins, if an excess amount of the organic solvent is mixed, the proteins may be coagulated and they cannot be filtered and as a result, the number of proteins contained in the fractionated solution may possibly be decreased very significantly.

Accordingly, it is requested to add the organic solvent to an extent that proteins are not coagulated and consequently, while adsorption of proteins in the hollow fiber membrane, the fluid channel, the recovery container, and the like is suppressed, the recovery ratio of the proteins can considerably be improved.

The organic solvent to be used in the invention is required to be soluble in a water-based buffer solution and usable examples of the solvent may include nitrogen-containing compounds such as acetonitrile and pyridine; cyclic ether compounds such as 1,4-dioxane and propylene oxide; ketone compounds such as acetone and ethyl methyl ketone; amides such as N,N-dimethylfomamide, N,N-dimethylacetamide, N,N'-dimethyl-2-imidazolidinone, and N-methyl-2-pyrrolidone; sulfur-containing compounds such as sulfolan and dimethyl sulfoxide; monohydric alcohols such as methanol, ethanol, and 2-propanol; cellosolves such as 2-methoxyethanol (methylcellosolve) and 2-ethoxyethanol (ethylcellosolve); ethanol amines such as 2-aminoethanol (monoethanol amine), diethanolamine, and triethanolamine; and polyhydric alcohols such as ethylene glycol, propylene glycol, diethylene glycol, and glycerin and among them are non-alcohol type organic solvents preferable to be used. One or more kinds of the organic solvents may be added to the buffer solution.

The boiling point of the organic solvent in the invention is preferably 100° C. or lower, more preferably 80° C. or lower, and even more preferably 60° C. or lower. As the boiling point is lower, the solvent removal by freeze drying and an evaporator becomes easier and if the operation is carried out at a low temperature at the time of the solvent removal, deformation of the proteins is suppressed to the minimum limit and therefore, it is preferable.

In the invention, addition of a water-soluble organic solvent to the buffer solution is most preferable. Herein, the buffer solution means a solution having a buffering function, that is, a solution which does not cause sharp pH alteration when being mixed with the protein solution. Accordingly, since simple water does not have the buffering function, it cannot be said that water is a buffer solution. As a composition of the buffer solution in the invention, a carbonate solution, a dicarbonate buffer solution, a phosphate buffer solution, and an acetate buffer solution are preferably to be used. In consideration of the possibility of execution of sample concentration by removing the solvent component by a freeze drying device or an evaporator in the case of mass-spectrometry after fractionation of proteins, it is preferable for the buffer solution in the invention to be volatile since salts do not remain in the sample. Those which satisfy the above-mentioned condition are buffer solution produced using ammonium salts and examples of the buffer compositions are ammonium hydrogen carbonate-ammonium carbonate, acetic acid-ammonium acetic acid, and formic acid-ammonium formate. When a sample obtained by fractionation using, for example, an ammonium hydrogen carbonated buffer solution is freeze-dried, the ammonium salt is evaporated in form of ammonia, carbon dioxide, and water.

The salt concentration of the buffer solution for the protein fractionation device of the invention is not particularly limited, however it is preferably 1 mM to 1 M and more preferably 10 mM to 100 mM. The hydrogen ion concentration (pH) of the buffer solution for the protein fractionation device of the invention is preferably 4.0 to 8.0. If pH is lower than 4.0 or higher than 8.0, deformation of the proteins becomes significant and therefore it is not preferable.

A separation membrane is used in the method of the invention and a hollow fiber membrane is preferable to be used. The material of the hollow fiber membrane is not particularly limited, however one or more kind materials containing polymers selected from a group consisting of cellulose, cellulose acetate, polycarbonates, polysulfones, polymethacrylates such as poly(methylmethacrylate), polyacrylates, polyamides, poly(vinylidene fluoride), polyacrylonitrile, polyesters, polyurethanes, polystyrenes, polyethylene, and polypropylene may be employed. With respect to the membrane structure, both having a sponge structure almost an uniform structure and having a double structure of a dense layer and a support layer having a high porosity and a high membrane strength may be used. The surface properties of the membrane are determined in accordance with the properties of proteins to be separated and may be hydrophilic or hydrophobic.

The hydrophilic membrane may include those produced by copolymerizing hydrophilic monomers and hydrophobic monomers or blending and film-forming hydrophilic polymers and hydrophobic polymers; those produced by bonding or sticking hydrophilic polymers to the surfaces of membranes of hydrophobic polymers; and those produced by chemically treating, plasma treating or radiation-treating the surfaces of membranes of hydrophobic polymers and if the surfaces are made hydrophilic, the method for the treatment is not particularly limited. The hydrophilic components are not particularly limited and preferable examples may include hydrophilic polymers, e.g., polyalkylene oxides such as polyethylene glycol, polyvinylpyrrolidone, polyvinyl alcohol, poly(hydroxyethyl methacrylate), and polyacrylamide. These hydrophilic membranes are effective to suppress adsorption of needed proteins and recover them without vain loss.

Further, materials in which one or more of polyethyleneimine, aminomethylpyridine, polyphenol, Blue dye, a divalent metal ion ($Zn^{2+}$ $Ni^{2+}$, $Co^{2+}$, $Cu^{2+}$, or the like), a hydrophobic compound (i.e. compound with methyl group, benzyl group, phenyl group, chloromethyl group, octyl group, lauryl group or the like), an antibody and its fragments are fixed may also be used.

With respect to the molecular fractionation capability of the membrane, membranes having a molecular weight fractionation capability (cut-off value: 30 to 60 kDa or lower) that is sufficient to prevent permeation of 50% or more albumin in physiological saline solution may be used.

In the invention, it is preferable to use a module filled with the above-mentioned hollow fiber membrane and the module is preferable to be provided with an inlet and an outlet through which a solution to be separated flows in and flows out and a separated solution outlet through which a separated solution flows out.

Herein the membrane packed in the housing of the module is preferable not to be isolated at the time of packing or leaking eluted substances derived from the packed material.

In the case of treating a protein solution by the method of the invention, it is also preferable to combine modules in multi-steps. Accordingly, high molecular weight proteins which cannot be removed completely by one module may be removed by the module in the next step and the S/N ratio of analysis data of the sample after fractionation treatment can be improved. These modules may be connected in series or in parallel.

It is also preferable to concentrate the protein solution obtained in the prior step after the fractionation by the method of the invention. In this case, concentration may be carried out using the membrane. The fractionation molecular weight of the membrane is preferably selected in accordance with the molecular weight of the proteins to be recovered. The fractionation molecular weight in this specification is an index to be employed for evaluating the capability of the filtration membrane and expressed as the molecular weight of a solute in a solution for which the apparent stopping ratio becomes 0.9 in the case filtration is carried out by the membrane. Since the membrane has the pore diameter distribution and practically molecules larger than the fractionation molecular weight can often pass the membrane, the fractionation molecular weight of the membrane to be used is preferably ½ to ¼ of the smallest molecular weight in a group of the proteins to be recovered. If the fractionation molecular weight of the membrane is too high, the proteins to be recovered are leaked to lower the recovery ratio in some cases and on the contrary, if it is too low, the permeability is lowered to increase the pressure and decrease the treatment speed in some cases. The morphology of the concentration membrane is not particularly limited, however a hollow fiber membrane is preferable to be used since it has sharp pore distribution and a high concentration efficiency as compared with a plane membrane.

In the case of fractionation of a protein solution by the method of the invention, it is preferable to carry out the treatment at a low temperature. By decreasing the temperature to low, the protease activity in the protein solution is decreased and the efficiency is improved high. The treatment temperature at the time of fractionation is preferably lower than 30° C., more preferably 0 to 20° C., and even more preferably 2 to 10° C. Not only the activity of the protease contained in serum or plasma is suppressed to prevent decomposition of proteins but also evaporation of the organic solvent is suppressed as much as possible by treatment at a low temperature. Particularly, in the case fractionation treatment is carried out using the hollow fiber membrane as in the invention, it is preferable to carry out the treatment at a low temperature in order to prevent an adverse effect of bubbles to be formed by evaporation of the organic solvent on the membrane separation capability.

EXAMPLES

At first, Examples of the first invention will be described.

Example A

First Invention

Figure 2:
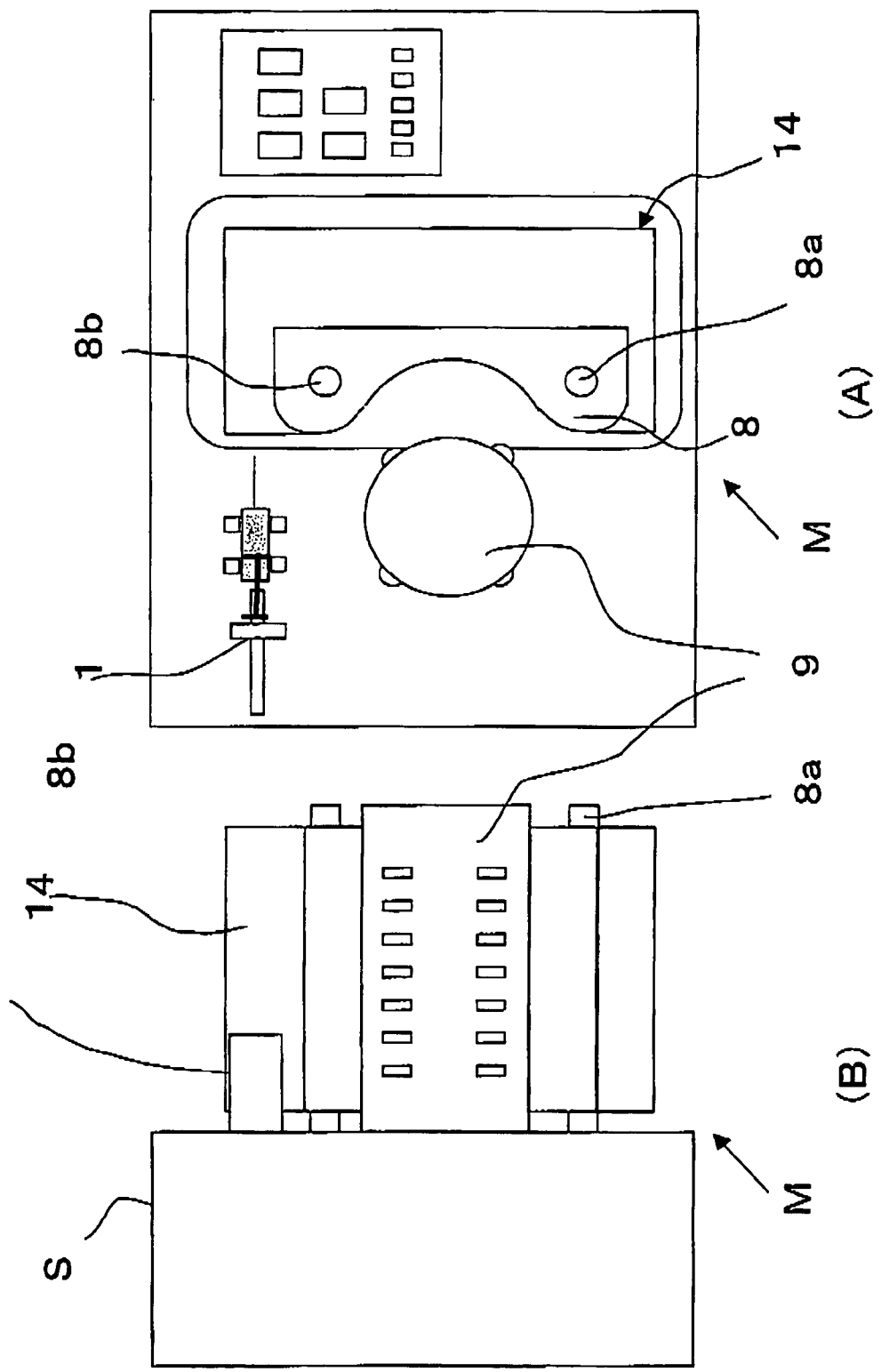
FIG. 2. A front view and a left side face view of the device used for Example 1 (for the first invention).

FIGS. 1 and 2 are explanatory drawing of a fractionation device of the invention. FIG. 1 shows the separation part is composed of three modules.

In FIG. 1, a three-way joint 2a and a joint 2c are connected to the rubber button 2b corresponding to the supply part. A flexible tube 3 connects the joint 2c and a lower nozzle 6a of hollow fiber membrane module 5a of the filtration part along the curved face of a multi-channel type squeezing member 8. Further a tube-equipped bag 12 is connected to the three-way joint 2a. Flexible tubes are connected to respective upper nozzles 4a, 4b, 4c, and 4d installed on the squeezing member, the filtration part hollow fiber membrane modules 5a, 5b, and 5c and a concentration part 5d. These tubes are laid along the curved face of the multi-channel type squeezing member 8 and respectively connected with the lower nozzles 6a, 6b, 6c, and 6d. Tubes are connected between a trunk lower nozzle 7a of the separation part hollow fiber membrane module 5a and the lower nozzle 6b of a hollow fiber membrane module 5b; between a trunk lower nozzle 7b of the separation part hollow fiber membrane module 5b and the lower nozzle 6c of a hollow fiber membrane module 5c; and between a trunk lower nozzle 7c of the separation part hollow fiber membrane module 5c and the lower nozzle 6d of a hollow fiber membrane module 5d. A trunk lower nozzle 7d of the hollow fiber membrane module 5d and the three-way joint 2a are connected by a tube. Further, the lower nozzle 6d of the hollow fiber membrane module 5d and a recovery container cap 11 of a recovery container 10 are connected with a tube. The upper nozzle 4d of the hollow fiber membrane module 5d and the recovery container cap 11 are also connected with each other. All of the above-mentioned hollow fiber membrane modules, nozzles, tubes, joint, tube-equipped bag, recovery container, and recovery container cap form a closed circuit.

At the time of fractionation, the closed circuit is filled with a water-based buffer solution as a mobile phase. The above-mentioned circuit is housed in a cartridge.

FIG. 2 is a drawing of the entire body of a fractionation device of the invention. FIG. 2A is a front view and FIG. 2B is a left side view. The device 14 is provided with a multi-channel type rotary roller 9. Guide shafts 8a and 8b formed in device main body side are inserted into the guide holes formed in the side face of the squeezing member 8 existing in the cartridge 14 and the cartridge 14 is pushed down to fix the cartridge in the device. The fixed cartridge 14 is moved in parallel toward the multi-channel type rotary roller 9 to form a flow system comprising the multi-channel type rotary roller 9, a rotor, the squeezing member 8, seven tubes laid along the curved face of the squeezing member 8.

Further, a syringe 1 is attached. Driving mechanisms connected to a motor are attached to the respective rotary rollers of the multi-channel type rotary roller 9.

Further explanation will be given with reference to FIG. 1 again. The flow of a liquid is shown by the arrow. After the needle of a syringe 1 enclosing a raw liquid such as serum is stuck to the rubber button 2b of the supply part, the sample is loaded at a prescribed speed by the syringe pump. After the loading, the syringe 1 is pulled out of the rubber button 2b. While being mixed with the mobile phase, the loaded raw liquid is transported to the separation part hollow fiber membrane module 5a by rotation of the rotary roller 9a driven by the motor. The filtrate produced during the circulation in the hollow fiber membrane module 5a by the rotation of the rotary roller 9b driven by the motor flows out of the trunk lower nozzle 7a and transported to the separation part hollow fiber membrane module 5b in the next stage by the rotation of the rotary roller 9b. The filtrate of the separation part hollow fiber membrane module 5b is further transported to the separation part hollow fiber membrane module 5c in the next but one stage.

In this manner, the solutes of the raw liquid are fractionated by the hollow fiber membrane modules 5a, 5b, and 5c composing the separation part. The filtrate from the hollow fiber membrane module 7c is transported to the concentration part hollow fiber membrane module 7d. The filtrate produced during the circulation in the hollow fiber membrane module 7d flows out of the trunk nozzle 7a and turned back to the supply part via the joint 2a. The filtrate of the hollow fiber membrane module 7c is transported to the concentration part hollow fiber membrane module 7d. The circulation and transportation of the liquids in the separation part and the concentration part are carried out by the rotary roller 9b. After a prescribed time passes, the rotary rollers 9a and 9b are stopped and the rotary roller 9c driven by the motor is started. Consequently, air in the recovery container 10 pushes out the concentrated liquid in the circuit in the concentration part and the concentrated liquid is recovered in the recovery container 10 via the lower nozzle 6d.

Next, Examples of the second invention will be described.

Example 1

A hundred polysulfone hollow fibers were bundled and both ends were fixed in a glass tube type module case with an epoxy type potting agent in a manner the hollow parts of the hollow fibers were not closed to produce a mini-module. The mini-module had an inner diameter of about 7 mm and a length of about 17 cm and two dialysis ports similarly to a common hollow fiber membrane type dialyzer. The hollow fibers of the mini-module and the inside of the module were washed with distilled water.

After that, an aqueous PBS (Dulbecco PBS (−) manufactured by NISSUI PHARMACEUTICAL CO., LTD) solution was packed to obtain a hollow fiber membrane mini-module (hereinafter, referred to as mini-module 1 for short). After precipitates were removed from human serum (H1388, Lot 28H8550, manufactured by SIGMA) by centrifugation at 3000 rpm for 15 min, the resulting human serum was filtered with a 0.45 μm filter. One of the dialyzed liquid side of the mini-module 1 was caped and the other was connected with a silicone tube connected with a Peri-Star™ pump, which is a rotary type tube pump. The mini-module inlet corresponding to the liquid in the hollow fiber membrane inside and the mini-module outlet were connected with a silicone tube to make the liquid containing the serum circulated by the Peri-Star™ pump. Four mL of serum was filtered at a circulation flow rate of 5 L/min, filtrate flow rate of 0.2 mL/min at 20° C. for 4 hours (this step is equivalent to the step of separating aimed low molecular weight proteins to be recovered and aimed high molecular weight proteins to be discarded).

The amount of the liquid to be circulated was kept constant by adding PBS in amount corresponding to the decreased volumetric amount in the circulation circuit because of the filtration.

On the other hand, HiTrap NHS-activated (manufactured by Amersham Biosciences), which is a coupling column for ligand fixation, was made ready and used as a column without sticking no antibody. Then, 0.2 mL of the filtrate was applied and passed through the column.

The albumin concentration in the serum loaded at first was measured by Human Albumin ELISA Quantitation Kit (manufactured by BETHYL) to find it was 27800 μg/mL and the albumin concentration after 4 hour filtration was found to be 61 μg/mL. The concentration of α1-microglobulin in the serum before fractionation measured by SRL, Inc. was found to be 8.9 μg/mL and concentration of al-microglobulin in the filtrate obtained after 4 hours was 0.45 μg/mL. Accordingly, the α1-microglobulin the permeation ratio/albumin permeation ratio=about 23 and within a range from 1.5 or higher and 1000 or lower.

Example 2

An antibody of human albumin was fixed in HiTrap NHS-activated (manufactured by Amersham Biosciences), which is a coupling column for ligand fixation, to produce an antibody column. The types and the amounts of the antibodies used are as shown in Table 1. The No. of each column produced by fixing each antibody of the human albumin was used as it was assigned to each antibody of the human albumin.

TABLE 1

Species and amount of antibody

| No. | Anti human albumin antibody | amount |
|---|---|---|
| P | Goat Anti-Human Albumin, Policlonal Antibody; Affinity Purified (Academy Bio-Medical Company, Inc.) | 0.5 mg |
| Q | Mouse Monoclonal Antibody to Human Serum Albumin, Clone: ZMHSA1 (ZYMED Laboratories Inc.) | 0.5 mg |
| R | IgG Fraction Rabbit Anti-Human Albumin (INTRE-CELL TECHNOLGIES, INC.) | 6.95 mg |
| S | Monoclonal Anti-Human Serum Albumin, Clone: 12D12 (Seradym) | 1 mg |
| T | Monoclonal Anti-Human Albumin, Clone: HSA1/25.1.3 (CEDARLANE Laboratories Limited) | 0.5 ml (concentration unknown) |

Each 0.2 mL of the filtrate obtained in Example 1 was applied to each of the following five types antibody columns and the solution passed through each column was obtained as a passed fractionation sample. The albumin concentration in each passed fractionation sample was measured by Human Albumin ELISA Quantitation Kit (manufactured by BETHYL). The results are shown in Table 2. The column numbers shown in Table 2 correspond to the antibody numbers used in Table 1.

TABLE 2

Amount of albmin adsorped to antibody column

| No. | feed amount | amount in flow through fraction | amount in adsorpted fraction |
|---|---|---|---|
| , | 12.2 ƒ g | ≤0.001 ƒ g | 12.2 ƒ g |
| , | 12.2 ƒ g | 0.016 ƒ g | 12.2 ƒ g |
| , | 12.2 ƒ g | 0.099 ƒ g | 12.1 ƒ g |
| , | 12.2 ƒ g | 0.251 ƒ g | 11.9 ƒ g |
| , | 12.2 ƒ g | ≤0.001 ƒ g | 12.2 ƒ g |

The albumin adsorbed in each of the columns was eluted by 0.1 M glycin hydrochloriate buffer solution (pH2.7) to obtain adsorbed fraction. The passed fractions and the adsorbed fractions were respectively concentrated to 0.2 mL by using a centrifugal separation membrane (vivaspin, 3000MWCO, manufactured by Sartorius AG) to obtain samples and 5 μL each of the samples were analyzed by SDS-PAGE. The analysis results are shown in FIG. 4.

Figure 4:
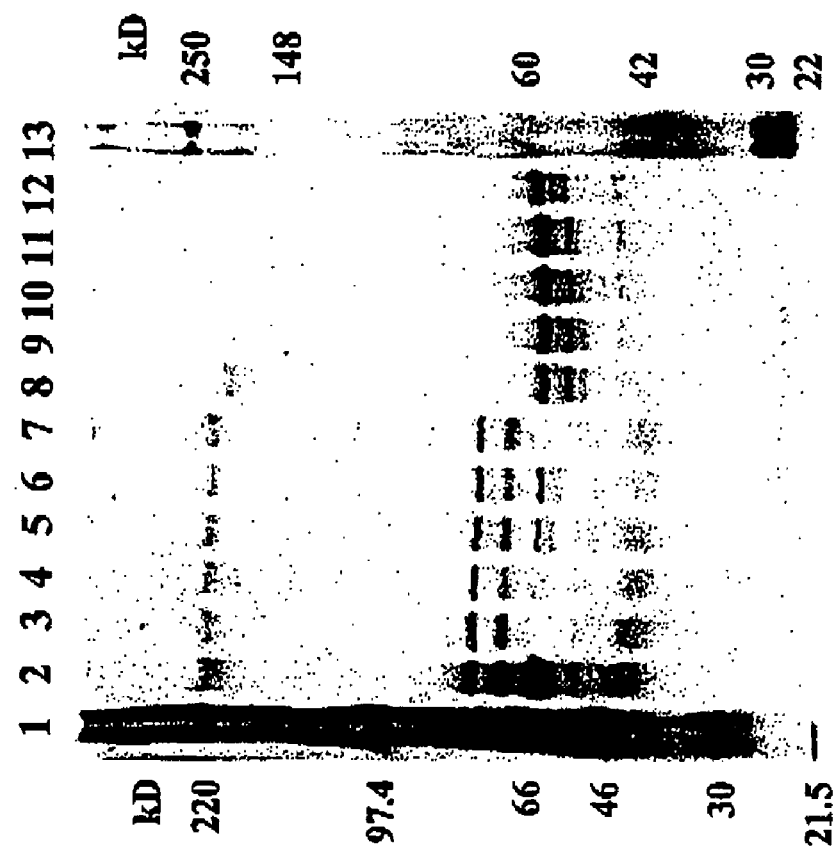
FIG. 4. A photograph of electrophoresis (SDS-PAGE) of respective fractions obtained in Example 2 (for the second invention).

FIG. 4 is a photograph of electrophoresis (SDS-PAGE) of each fraction obtained in Example 2. The respective lanes of FIG. 4 are as follows.

Lane 1: a rainbow marker, a molecular weight marker for electrophoresis (RPN756, manufactured by Amersham)

Lane 2: the filtrate obtained in Example 1

Lane 3: the fraction passing through the column No. 1

Lane 4: the fraction passing through the column No. 2

Lane 5: the fraction passing through the column No. 3

Lane 6: the fraction passing through the column No. 4

Lane 7: the fraction passing through the column No. 5

Lane 8: the fraction adsorbed in the column No. 1

Lane 9: the fraction adsorbed in the column No. 2

Lane 10: the fraction adsorbed in the column No. 3

Lane 11: the fraction adsorbed in the column No. 4

Lane 12: the fraction adsorbed in the column No. 5

Lane 13: MultiMark, a molecular weight marker for electrophoresis (LC 5725, manufactured by Invitrogen)

From FIG. 4 is understood that albumin exists in a large quantity in the respective sample before the antibody column treatment disappears almost completely from the fractions passed through the columns and accordingly the proteins were decreased to 10% or lower or scarcely exist in the passed fractions owing to the existence of the albumin antibodies.

Example 3

A half of the filtrate obtained in the process of Example 1 was concentrated to 1 mL by a centrifugal separation type membrane (vivaspin, 3000MWCO, manufactured by Sartorium AG), mixed with 4 mL of a buffer solution exclusively for the column (Buffer A No. 5185-5987, manufactured by Agilent), filtered by a centrifugal filter with 0.22 μm size, and separated by affinity columns in which 6 type antibodies were combined, Multiple Affinity Removal Column (No. 5185-5985, manufactured by Agilent).

Solutions containing components with weal affinity with the columns obtained by 5 mL or more Buffer A was passed after sample application were recovered as passed fractions.

Next, the proteins adsorbed in the columns were eluted by a buffer for elution exclusively for the columns (BufferB No. 5185-5988, manufactured by Agilent) to obtain adsorbed fractions. The passed fractions and the adsorbed fractions were respectively concentrated to 1 mL by the centrifugal separation type membrane (vivaspin, 3000MWCO, manufactured by Sartorius AG) and each 10 µL of the obtained fractions were analyzed by SDS-PAGE. The positions of the bands separated from the passed fractions and the positions of the bands separated from the adsorbed fractions were scarcely overlapped and owing to the existence of the antibodies, the proteins were suppressed to 10% or lower and scarcely observed.

Comparative Example 1

The human serum of the same lot as that of Example 1 (H1388, Lot 28H8550, manufactured by SIGMA) in an amount of 40 µL was distilled 5 times by the buffer solution exclusively for the antibody columns employed in Example 3 and separated. The passed fractions and the adsorbed fractions were respectively concentrated to 1 mL by the centrifugal separation type membrane (vivaspin, 3000MWCO, manufactured by Sartorius AG) and each 10 µL of the obtained fractions were analyzed by SDS-PAGE. According to the analysis results, some bands of albumin or others disappeared by the antibodies, however bands in a wide range covering from a high molecular weight substance to a low molecular weight substance were found existing.

Hereinafter, Examples of the third invention will be described.

Example 4

Hollow fiber membranes made of polysulfone were obtained by cutting resin adhesion parts in both ends of a blood dialyzer (TS 1.6 ML, manufactured by Toray Industries, Inc.). The size of the obtained hollow fiber membrane was an inner diameter of 200 µm and a membrane thickness of 40 µm and the cross-sectional shape where a liquid is passed was found having an asymmetric structure by observation. A hundred of the polysulfone hollow fibers were bundled and both ends were fixed in a glass tube type module case with an epoxy type potting agent in a manner the hollow parts of the hollow fibers were not closed to produce a mini-module. The mini-module had an inner diameter of about 7 mm and a length of about 17 cm and had each two ports (circulation ports) for circulating a liquid in the hollow fibers and dialysis ports similarly to a common hollow fiber membrane type dialyzer. The hollow fiber membranes of the mini-module and the inside of the module were washed with distilled water.

Ammonium hydrogen carbonate (manufactured by Sigma-Aldrich Japan) and ammonium carbonate were respectively dissolved in milli-Q water and both were mixed to adjust pH 8.0 and obtain 50 mM ammonium hydrogen carbonate buffer solution (pH 8.0) (hereinafter, simply referred to buffer solution A). Acetonitrile (high performance liquid chromatography, manufactured by Sigma-Aldrich Japan) in an amount proper to adjust the acetonitrile concentration to be 10% (v/v) was added and well stirred to obtain a buffer solution for protein fractionation of the invention (hereinafter, referred to 10% acetonitrile-added buffer solution A).

The following process was carried out at a low temperature chamber set at 4° C. T-shape tubes were assembled at two point of one silicon tube with a whole length of 65 cm (inner diameter 2 mm and outer diameter 4 mm, manufactured by ASONE CO., LTD.) (silicone tube A) and a pressure gauge was connected to an aperture part of a first T-shape tube which was not connected to the silicon tube A via a silicon tube (silicon tube B). A syringe was connected to an aperture part of a second T-shape tube which was not connected to the silicon tube A via a silicon tube (the whole length 15 cm, inner diameter 2 mm, and outer diameter 4 mm) (silicon tube C) to form a liquid injection inlet. The syringe was filled with the 10% acetonitrile-added buffer solution A and installed in a micro-syringe pump (hereinafter referred to as syringe pump, manufactured by KD Scientific) and a rotary type micro-tube pump (hereinafter referred to flow pump, manufacture by Tokyo Rika Kiki Co., Ltd.) was installed in the middle of the silicon tube between the two T-shape tubes. After the silicon tube B connected to the pressure gauge and the silicon tube C connected to the syringe were stopped by forceps and then one end of the silicon tube A was immersed in a container containing the 10% acetonitrile-added buffer solution A and the flow pump was operated to fill the silicon tube A with the 10% acetonitrile-added buffer solution A and the flow rate was adjusted to be at 5 mL/min.

One end of the circulation port of the mini-module was connected with one end of the above-mentioned silicon tube A and the flow pump was operated to send the 10% acetonitrile-added buffer solution A to the inside of the hollow fiber membrane and the bubbles in the inside hollow part were removed. After the flow pump was stopped, the other end of the silicon tube A was connected with the end part of the module. In such manner, a circulation circuit in which the module, syringe, and the pressure gauge were connected was formed. Human serum (manufactured by Sigma) diluted 4 times with 10% acetonitrile-added buffer solution A (hereinafter referred to as diluted serum A) 4.5 mL was taken by the syringe and a wing-attached injection needle (manufactured by Terumo) was attached to the syringe and set in a micro-syringe pump. After the diluted serum A was injected up to the tip end of the needle and it was confirmed that there was no bubbles, the tip end of the injection needle was inserted into the liquid injection inlet formed near the T-shape tube in which the silicon tube B was installed in the circuit to connect the needle with the circuit and thus complete the protein fractionation device.

After the 10% acetonitrile-added buffer solution A was circulated at 5 mL/min by operating the flow pump, the syringe pump was operated to push out the diluted serum A at 0.2 mL/min to start fractionation treatment. In this case, the filtered solution from the module was recovered in a 50 mL-capacity sedimentation tube made of polypropylene. After 20 minutes, the syringe pump was stopped at the time when 4 mL of the diluted serum was pushed out and immediately the syringe pump to which the syringe filled with the 10% acetonitrile-added buffer solution A was attached was operated at 0.2 mL/min to continue the treatment. After 120 minutes from starting the fractionation, the syringe pump and the flow pump were both stopped. At that time, the volume of the recovered solution passing the membrane and recovered was about 24 mL. The recovered solution was freeze dried and dissolved again in the buffer solution A. The respective concentrations of the human serum albumin (HSA), β2-microglobulin (β2MG), and interleukin-8 (IL-8) were measured by an enzyme-linked immunosorbent assay (ELISA). As a result, as shown in Table 3, the recovery ratio of HSA, an object to be removed was as extremely low as 0.009% in the content contained in the diluted serum A, meanwhile β2MG and IL-8, objects to be recovered, were recovered at 51.2% and 17.4%, respectively.

TABLE 3

Table. 3

| | Recovery (%) | | |
|---|---|---|---|
| | HSA | 2MG | IL-8 |
| Example 4 | 0.009 | 51.2 | 17.4 |
| Example 5 | 0.012 | 52.3 | 19.7 |
| Example 6 | 0.028 | 54.3 | 24.3 |
| Example 7 | 0.039 | 55.9 | 25.1 |
| Example 8 | 0.008 | 41.9 | 17.1 |
| Example 9 | 0.007 | 34.1 | 16.2 |
| Example 10 | 0.004 | 20.5 | 11.7 |
| Example 11 | 0.035 | 9.4 | 13.2 |
| Example 12 | 0.022 | 58.7 | 20.5 |
| Example 13 | 0.037 | 57.5 | 21.2 |
| Example 14 | 0.023 | 46.8 | 18.9 |
| Comparative example 2 | N.D. | 5.90 | N.D. |
| Comparative Example 3 | N.D. | N.D. | 1.83 |

N.D. The result of measurement is below detection sensitivity.

Example 5

Acetonitrile (high performance liquid chromatography, manufactured by Sigma-Aldrich Japan) in an amount proper to adjust the acetonitrile concentration to be 12.5% (v/v) was added and well stirred and degassed to obtain a buffer solution for protein fractionation of the invention (hereinafter, referred to 12.5% acetonitrile-added buffer solution A). Human serum (manufactured by Sigma) diluted 4 times with the 12.5% acetonitrile-added buffer solution A (hereinafter, referred to as diluted serum B) in an amount of 4 mL was treated by the module in the same manner as Example 4. As a result, as shown in Table 3, the recovery ratio of HSA, an object to be removed was as extremely low as 0.012% in the content contained in the diluted serum B, meanwhile β2MG and IL-8, objects to be recovered, were recovered at 52.3% and 19.7%, respectively.

Example 6

Acetonitrile (high performance liquid chromatography, manufactured by Sigma-Aldrich Japan) in an amount proper to adjust the acetonitrile concentration to be 15% (v/v) was added and well stirred and degassed to obtain a buffer solution for protein fractionation of the invention (hereinafter, referred to 15% acetonitrile-added buffer solution A). Human serum (manufactured by Sigma) diluted 4 times with the 15% acetonitrile-added buffer solution A (hereinafter, referred to as diluted serum C) in an amount of 4 mL was treated by the module in the same manner as Example 4. As a result, as shown in Table 3, the recovery ratio of HSA, an object to be removed was as extremely low as 0.028% in the content contained in the diluted serum C, meanwhile β2MG and IL-8, objects to be recovered, were recovered at 54.3% and 24.3%, respectively.

Example 7

Acetonitrile (high performance liquid chromatography, manufactured by Sigma-Aldrich Japan) in an amount proper to adjust the acetonitrile concentration to be 17.5% (v/v) was added and well stirred and degassed to obtain a buffer solution for protein fractionation of the invention (hereinafter, referred to 17.5% acetonitrile-added buffer solution A). Human serum (manufactured by Sigma) diluted 4 times with the 17.5% acetonitrile-added buffer solution A (hereinafter, referred to as diluted serum D) in an amount of 4 mL was treated by the module in the same manner as Example 4. As a result, as shown in Table 3, the recovery ratio of HSA, an object to be removed was as extremely low as 0.039% in the content contained in the diluted serum D, meanwhile β2MG and IL-8, objects to be recovered, were recovered at 55.9% and 25.1%, respectively.

Example 8

Acetonitrile (high performance liquid chromatography, manufactured by Sigma-Aldrich Japan) in an amount proper to adjust the acetonitrile concentration to be 7.5% (v/v) was added and well stirred and degassed to obtain a buffer solution for protein fractionation of the invention (hereinafter, referred to 7.5% acetonitrile-added buffer solution A). Human serum (manufactured by Sigma) diluted 4 times with the 7.5% acetonitrile-added buffer solution A (hereinafter, referred to as diluted serum E) in an amount of 4 mL was treated by the module in the same manner as Example 4. As a result, as shown in Table 3, the recovery ratio of HSA, an object to be removed was as extremely low as 0.008% in the content contained in the diluted serum E, meanwhile β2MG and IL-8, objects to be recovered, were recovered at 41.9% and 17.1%, respectively.

Example 9

Acetonitrile (high performance liquid chromatography, manufactured by Sigma-Aldrich Japan) in an amount proper to adjust the acetonitrile concentration to be 5.0% (v/v) was added and well stirred and degassed to obtain a buffer solution for protein fractionation of the invention (hereinafter, referred to 5.0% acetonitrile-added buffer solution A). Human serum (manufactured by Sigma) diluted 4 times with the 5.0% acetonitrile-added buffer solution A (hereinafter, referred to as diluted serum F) in an amount of 4 mL was treated by the module in the same manner as Example 4. As a result, as shown in Table 3, the recovery ratio of HSA, an object to be removed was as extremely low as 0.007% in the content contained in the diluted serum F, meanwhile β2MG and IL-8, objects to be recovered, were recovered at 34.1% and 16.2%, respectively.

Example 10

Acetonitrile (high performance liquid chromatography, manufactured by Sigma-Aldrich Japan) in an amount proper to adjust the acetonitrile concentration to be 2.5% (v/v) was added and well stirred and degassed to obtain a buffer solution for protein fractionation of the invention (hereinafter, referred to 2.5% acetonitrile-added buffer solution A). Human serum (manufactured by Sigma) diluted 4 times with the 2.5% acetonitrile-added buffer solution A (hereinafter, referred to as diluted serum G) in an amount of 4 mL was treated by the module in the same manner as Example 4. As a result, as shown in Table 3, the recovery ratio of HSA, an object to be removed was as extremely low as 0.004% in the content contained in the diluted serum G, meanwhile β2MG and IL-8, objects to be recovered, were recovered at 20.5% and 11.7%, respectively.

Example 11

A 50 mM ammonium acetate buffer solution (pH 5.0) (hereinafter referred to as buffer solution B) was produced and acetonitrile (high performance liquid chromatography, manufactured by Sigma-Aldrich Japan) in an amount proper to adjust the acetonitrile concentration to be 10% (v/v) was added and well stirred and degassed to obtain a buffer solution for protein fractionation of the invention (hereinafter, referred to acetonitrile-added buffer solution B). Human serum (manufactured by Sigma) diluted 4 times with the acetonitrile-added buffer solution B (hereinafter, referred to as diluted serum H) in an amount of 4 mL was treated by the module in the same manner as Example 4. As a result, as shown in Table 3, the recovery ratio of HSA, an object to be removed was as extremely low as 0.035% in the content contained in the diluted serum H, meanwhile β2MG and IL-8, objects to be recovered, were recovered at 9.4% and 13.2%, respectively.

Example 12

1,4-Dioxane (manufactured by Sigma-Aldrich Japan) in an amount proper to adjust the concentration to be 10% (v/v) was added and well stirred with the buffer solution A (hereinafter referred to as dioxane-added buffer solution A). Human serum (manufactured by Sigma) diluted 4 times with the dioxane-added buffer solution A (hereinafter, referred to as diluted serum I) in an amount of 4 mL was treated by the module in the same manner as Example 4. As a result, as shown in Table 3, the recovery ratio of HSA, an object to be removed was as extremely low as 0.022% in the content contained in the diluted serum I, meanwhile β2MG and IL-8, objects to be recovered, were recovered at 58.7% and 20.5%, respectively.

Example 13

Acetone (manufactured by Sigma-Aldrich Japan) in an amount proper to adjust the concentration to be 10% (v/v) was added and well stirred with the buffer solution A (hereinafter referred to as acetone-added buffer solution A). Human serum (manufactured by Sigma) diluted 4 times with the acetone-added buffer solution A (hereinafter, referred to as diluted serum J) in an amount of 4 mL was treated by the module in the same manner as Example 4. As a result, as shown in Table 3, the recovery ratio of HSA, an object to be removed was as extremely low as 0.037% in the content contained in the diluted serum I, meanwhile β2MG and IL-8, objects to be recovered, were recovered at 57.5% and 21.2%, respectively.

Example 14

Ethanol (manufactured by Sigma-Aldrich Japan) in an amount proper to adjust the concentration to be 10% (v/v) was added and well stirred with the buffer solution A (hereinafter referred to as ethanol-added buffer solution A). Human serum (manufactured by Sigma) diluted 4 times with the ethanol-added buffer solution A (hereinafter, referred to as diluted serum J) in an amount of 4 mL was treated by the module in the same manner as Example 4. As a result, as shown in Table 3, the recovery ratio of HSA, an object to be removed was as extremely low as 0.023% in the content contained in the diluted serum I, meanwhile β2MG and IL-8, objects to be recovered, were recovered at 46.8% and 18.9%, respectively.

Comparative Example 2

The buffer solution A was injected in the circuit and human serum (manufactured by Sigma) diluted 4 times with the buffer solution A (hereinafter, referred to as diluted serum L) in an amount of 4 mL was injected at 0.2 mL/min in the circuit and fractionated in the same manner as Example 4. As a result, as shown in Table 3, the recovery ratio of HSA, an object to be removed was so low as to be the detection limit or lower, however β2MG and IL-8, objects to be recovered, were recovered at 5.90%, respectively, also so low as to be the detection limit.

Comparative Example 3

The buffer solution B was injected in the circuit and human serum (manufactured by Sigma) diluted 4 times with the buffer solution A (hereinafter, referred to as diluted serum M) in an amount of 4 mL was injected at 0.2 mL/min in the circuit and fractionated in the same manner as Example 4. As a result, as shown in Table 3, the recovery ratio of HSA, an object to be removed was so low as to be the detection limit or lower, however β2MG and IL-8, objects to be recovered, were recovered as low as 1.83%, respectively.

Comparative Example 4

The buffer solution A was injected in the circuit and human serum (manufactured by Sigma) diluted 4 times with the buffer solution A (hereinafter, referred to as diluted serum N) in an amount of 4 mL was injected at 0.2 mL/min in the circuit and fractionated in the same manner as Example 4, except that the treatment temperature was set at 30° C. As a result, bubbles were formed during the treatment and the evaluation was impossible.

INDUSTRIAL APPLICABILITY

These inventions are very useful for producing samples for proteome analysis and remarkably advantageous in medical spheres and particularly diagnosis of human diseases.

What is claimed is:

1. A fractionation device for separating one or more solutes from a raw liquid with a membrane comprising:
    1) a supply part for loading the raw liquid;
    2) a filtration part connected to the supply part by a flow channel for filtering out one or more solutes from the raw liquid received from the supply part to produce a filtrate;
    3) a concentration part connected to the filtration part by a flow channel for increasing the concentration of one or more solutes in the filtrate received from the filtration part to produce a concentrated solution;
    4) a recovery part connected to the concentration part by a flow channel for recovering the concentrated solution obtained in the concentration part; and
    5) one or more flow pumps operatively connected to one or more of the supply part, filtration part and concentration part for moving liquid through the fractionation device,
      wherein the filtration part, the concentration part, and the flow channel connecting the filtration part and the concentration part form a closed circuit; and
      wherein at least a portion of the circuit composed of the supply part, the filtration part, the concentration part, the recovery part, and flow channels connecting the respective parts is assembled in a cartridge,
      the flow pump is a tube pump provided with a rotating rotor and a roller installed in a rotating manner in the outer circumference of the rotor, and
      a portion of the outer wall of the cartridge is a squeezing member for squeezing a part of the flow channels of the circuit.

2. The fractionation device as claimed in claim 1, wherein the supply part, the filtration part, and the flow channel connecting the supply part and the filtration part form a closed circuit, and wherein the concentration part, the recovery part, and a flow channel connecting the concentration part and the recovery part form a closed circuit.

3. The fractionation device as claimed in claim 2, wherein the total inner capacity of the closed circuits is 50 mL or lower.

4. The fractionation device as claimed in claim 2, wherein a filtration apparatus is employed in each of the filtration part and the concentration part each.

5. The fractionation device as claimed in claim 4, wherein the filtration apparatus is a module having hollow fiber membranes.

6. The fractionation device as claimed in claim 5, wherein the flow channel connecting the supply part and the filtration part is provided with a pump.

7. The fractionation device as claimed in claim 6, wherein the recovery part is a container for sampling a concentrated liquid.

8. The fractionation device as claimed in claim 7, wherein a buffer part for buffering the volumetric alteration at the time of loading the raw liquid is installed at any position in the circuit.

9. A fractionation device as claimed in claim 5, wherein the module of the filtration part has a permeation ratio of human $\alpha_1$ microglobulin and human albumin (permeability of human $\alpha_1$ microglobulin/permeability of human albumin) in a range from 1.5 or higher to 1000 or lower under a condition that no antibody adsorbing proteins exist in the device, and an antibody capable of adsorbing specified proteins is contained in a middle or a rear part of the module of the filtration part.

10. The fractionation device as claimed in claim 9, wherein the specified proteins are serum albumin, immunoglobulin G, immunoglobulin A, immunoglobulin M, transferrin, haptoglobin, $\alpha_1$-antitrypsin, $\alpha_2$-macroglobulin, $\alpha_1$-acid glycoprotein, fibrinogen, complement C1q, complement C3, complement C4, complement C8, complement C9, complement factor B, apolipoprotein A, apolipoprotein B, Lp(a), collagen, myosin, actin, cytokeratin, keratin, and/or fibronectin.

11. The fractionation device as claimed in claim 10, wherein the antibody is polyclonal antibody, monoclonal, or their fragments containing the antigen recognition sites.

12. The fractionation device as claimed in claim 11, wherein the antibody is fixed in the membrane surface of the module of the filtration part.

13. The fractionation device as claimed in claim 12, wherein the filtration part comprises columns containing hollow fiber therein and arranged in multi-step in series and the antibody is fixed in the surface in the raw liquid side of the membrane of the column in the first stage.

14. The fractionation device as claimed in claim 12, wherein the filtration part comprises columns containing hollow fiber therein and arranged in multi-step in series and the antibody is fixed in the surface in the permeation side of the separation membrane of the column in the first stage.

15. The fractionation device as claimed in claim 12, wherein the filtration part comprises columns containing hollow fiber therein and arranged in multi-step in series and the antibody exists in the mobile phase in the flow channel between the membrane of the column in a prior stage and the membrane of the column in a posterior stage.

16. The fractionation device as claimed in claim 12, wherein the filtration part comprises columns containing hollow fiber therein and arranged in multi-step in series and the antibody is fixed in the flow channel between the membrane of the column in a prior stage and the membrane of the column in a posterior stage.

17. The fractionation device as claimed in claim 1, wherein the fractionation device is provided with a transportation mechanism for transporting the cartridge in the direction to and from the rotor of the roller type tube pump to squeeze a flow pipe.

18. The fractionation device as claimed in claim 1, wherein the raw liquid is a body fluid or a biological component-containing solution.

19. A fractionation device comprising a cartridge and a roller type tube pump for separating solutes or some of the solutes in a raw liquid with a membrane,
wherein the cartridge comprises at least a portion of a circuit having at least a supply part for loading the raw liquid, a fractionation part connected with the supply part by a flow channel for fractionating solutes of the raw liquid by a membrane, and a recovery part connected with the fractionation part for recovering the fractionated solutes,
the circuit is a closed circuit,
a part of the outer wall of the cartridge is a squeezing member for squeezing a tube of the roller type tube pump, and
a tube forming a part of the circuit is disposed on a part of the outer wall of the squeezing member.

20. A circuit of a fractionation device for separating solutes or some of the solutes from a raw liquid with a membrane, wherein at least a portion of the circuit is contained within a cartridge and the circuit comprises a supply part for loading the raw liquid, a fractionation part connected with the supply part by a flow channel for fractionating solutes of the raw liquid with a membrane, and a recovery part connected with the fractionation part for recovering the fractionated solutes,
the circuit is a closed circuit,
a part of the outer wall of the cartridge forms a squeezing member, and
a tube forming a part of the circuit is disposed on a portion of the outer wall of the squeezing member.

* * * * *